US011266723B1

(12) United States Patent
Powell et al.

(10) Patent No.: US 11,266,723 B1
(45) Date of Patent: Mar. 8, 2022

(54) METHODS AND COMPOSITIONS FOR TREATING CORONAVIRUS INFECTIONS

(71) Applicant: MOREHOUSE SCHOOL OF MEDICINE, Atlanta, GA (US)

(72) Inventors: Michael Powell, Douglasville, GA (US); Erick Vidjin' Agnih Gbodossou, Dakar-Etoile (SN)

(73) Assignee: MOREHOUSE SCHOOL OF MEDICINE, Atlanta, GA (US)

( * ) Notice: Subject to any disclaimer, the term of this patent is extended or adjusted under 35 U.S.C. 154(b) by 0 days.

(21) Appl. No.: 17/342,897

(22) Filed: Jun. 9, 2021

Related U.S. Application Data

(63) Continuation-in-part of application No. 16/996,153, filed on Aug. 18, 2020.

(51) Int. Cl.

| | |
|---|---|
| ***C07K 16/10*** | (2006.01) |
| ***A61P 31/14*** | (2006.01) |
| ***A61K 39/00*** | (2006.01) |
| ***A61K 45/06*** | (2006.01) |
| ***A61K 39/15*** | (2006.01) |
| ***A61K 38/47*** | (2006.01) |
| ***A61K 9/00*** | (2006.01) |
| ***A61K 35/76*** | (2015.01) |
| ***A61K 36/42*** | (2006.01) |
| *A61K 48/00* | (2006.01) |

(52) U.S. Cl.
CPC ............ *A61K 38/47* (2013.01); *A61K 9/0053* (2013.01); *A61K 35/76* (2013.01); *A61K 36/42* (2013.01); *A61K 45/06* (2013.01); *A61P 31/14* (2018.01); *C12Y 302/01014* (2013.01); *A61K 48/00* (2013.01); *C12N 2750/14143* (2013.01)

(58) Field of Classification Search
CPC .... A61K 2236/00; A61K 36/42; A61K 38/10; A61K 9/0053; A61K 9/14; A61K 9/20; A61K 9/48; A61P 31/18; A61P 31/14; C07K 16/10; C07K 2317/565; C07K 2317/76; C07K 2317/92
See application file for complete search history.

(56) References Cited

U.S. PATENT DOCUMENTS

| | | | |
|---|---|---|---|
| 2002/0182272 | A1 | 12/2002 | Halstead |
| 2011/0229604 | A1 | 9/2011 | Real |
| 2012/0009286 | A1 | 1/2012 | Gbodossou |
| 2016/0238601 | A1 | 8/2016 | Baric et al. |
| 2018/0015063 | A1 | 1/2018 | Babu et al. |
| 2020/0197469 | A1 | 6/2020 | Powell et al. |

FOREIGN PATENT DOCUMENTS

| | | |
|---|---|---|
| WO | 02/062364 | 8/2002 |
| WO | 2016181214 | 11/2016 |

OTHER PUBLICATIONS

Gbodossou, E. V. A., The Efficacy of African Herbal Medicine (METRAFAIDS) in the Treatment of HIV Positive African Populations—Report of Clinical Observational Study, Prometra (Association for the Promotion of Traditional Medicine).
Vasisht, K. et al., "Compedium of Medicinal and Aromatic Plants", ICS Unido 2004, pp. 1-124.
Indigenous African Plant-Based Extracts provide promising preliminary results against Ebola Virus, www.msm.edu/RSSFeedArticles/AfricasAnswertoEbola.php, pp. 1-4.
Senegal: Traditional Medicine Treatment for Aids Passes Clinical Tests, allAfrica.com.
Amzat, J. et al., "Roles of Traditional Healers in the Fight Against HIV/AIDS", Ethno-Med., 2008, vol. 2(2), pp. 153-159.
Sun, Y. et al., "Mono-PEGylation of Alpha-MMC and MAP30 from Momordica charantia L.: Production, Identification and Anti-Tumor Activity", Molecules, 2016, vol. 21(11), pp. 1-9.
Kesari, P. et al., "Structural and functional evolution of chitinase-like proteins from plants", Proteomics, 2015, vol. 15, pp. 1693-1705.
Fan, X. et al., "A-MMC and MAP30, two ribosome-inactivating proteins extracted from Momordica charantia, induce cell cycle arrest and apoptosis in A549 human lung carcinoma cells", Mol. Med. Rep., 2015, vol. 11(5), pp. 3553-3558.
Schrot, J. et al., "Ribosome-inactivating and related proteins", Toxins, 2015, vol. 7(5), pp. 1556-1615.
Zhou, Y. et al., "A Single Asparagine-Linked Glycosylation Site of the Severe Acute Respiratory Syndrome Coronavirus Spike Glycoprotein Facilitates Inhibition by Mannose-Binding Lectin through Multiple Mechanisms", Journal of Virology, Sep. 2010, vol. 84(17), p. 8753-8764.
Raman, R. et al., "Glycan-Protein Interactions in Viral Pathogenesis", Curr Opin Struct Biol. Oct. 2016; vol. 40, pp. 153-162.
Akkouh, O. et al., "Lectins with Anti-HIV Activity: A Review", Molecules, 2015, vol. 20, pp. 648-668.
De Wit, E. et al., "SARS and MERS: recent insights into emerging coronaviruses", Microbiology, vol. 14, Aug. 2016, pp. 523-534.
Mani, J.S. et al., "Natural product-derived phytochemicals as potential agents against coronaviruses: A review", Virus Research 284, (2020), 197989.
Bitter, G.A., et al. "Expression and secretion vectors for yeast", Elsevier, Methods in Enzymology, vol. 153, 1987, pp. 516-544.

*Primary Examiner* — Barry A Chestnut
(74) *Attorney, Agent, or Firm* — Ping Wang; Rimon Law

(57) ABSTRACT

The present application relates to a compositions and methods comprising or expressing a HEVAR or MOMO30 protein derived from *Momordica balsamina*. The HEVAR or MOMO30 protein and/or a nucleic acid encoding the same may be used in methods for treating or preventing viral infections, particularly those caused by coronaviruses, such as SARS-CoV-2.

19 Claims, 8 Drawing Sheets

Specification includes a Sequence Listing.

```
┌─────────────────────────────────────┐
│   Dried plants extracted in water   │
└─────────────────────────────────────┘
                 ⇩
┌─────────────────────────────────────┐
│          Plant cells lysed          │
└─────────────────────────────────────┘
                 ⇩
┌─────────────────────────────────────┐
│ Plant cell lysate centrifuged to remove │
│        debris and particulates      │
└─────────────────────────────────────┘
                 ⇩
┌─────────────────────────────────────┐
│ Clarified plant cell lysates run through MW │
│ cut-off filter to sterilize and further purify │
│  MOMO30 or HEVAR protein in retentate │
└─────────────────────────────────────┘
                 ⇩
┌─────────────────────────────────────┐
│ MOMO30 or HEVAR-containing retentate │
│ resuspended in buffer for further analysis, │
│ immunoaffinity purification and/or storage │
└─────────────────────────────────────┘
```

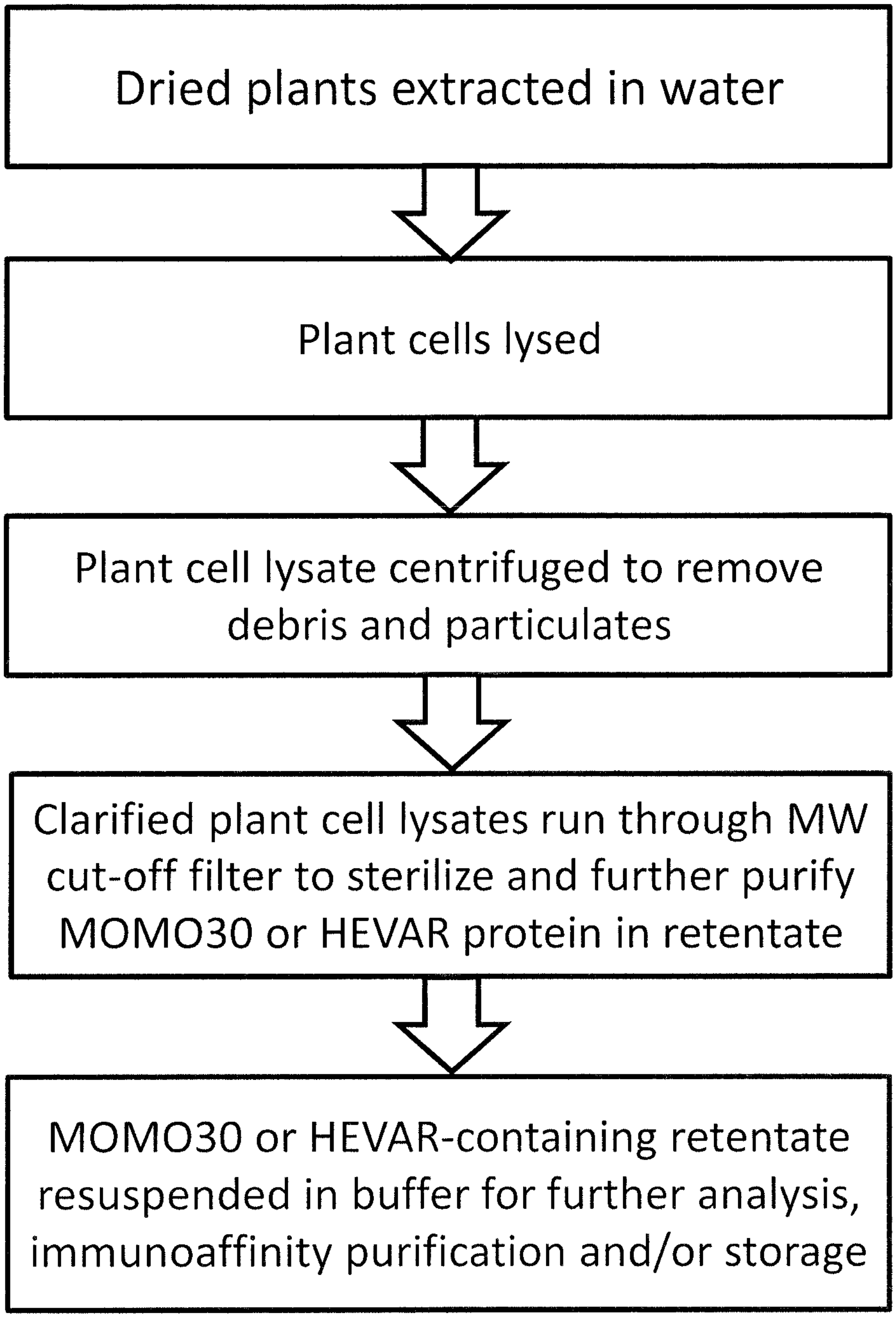

Signal peptide

```
                                        GPIVTYWGQNVXEGEL  SEQ ID NO:1
XP_028786671.1  MSSKTQALVLLLSPLLLLSHLSSSQGCPIVTYWGQNVNEGELSTACDTRKYEIINIAFMNTFGNGQTPNIDLSGHCSESW  80  SEQ ID NO:2
XP_028786682.1  MASKTQAFVLLLWPLLLLSHLSSSQSCPIVTYWGQNVNEGELDAACLTKRYEIINIAFMNTFGNGQTPDINLSGHCSESW  80  SEQ ID NO:3
XP_028773277.1  MSYKTQALVLLLSPLLLLSHLSSSQGCPIVTYWGQNVNEGELSTACDTGKYEIINIAFMNTFGNGQTPNIDLSGHCSESW  80  SEQ ID NO:4
XP_028773263.1  MSSKTQALVLLLSPLLLLSHLSSSQGYPIVTYWGQNVNEGELSTACDTGKYEIINIAFMNTFGNGQTPNIDLSGHCSESW  80  SEQ ID NO:5
XP_028773269.1  MSSKTQALVLLLSPLLLLSHLSSSQGCPIVTYWGQNVNEGELSTACDTGKYEIINIAFMNTFGNGQTPDINLAGHCSASW  80  SEQ ID NO:6
XP_028786677.1  MASKTQALVLLLWPLMLLSHLSSSQSCPIVTYWGQNVNEGELDAACQTEKYEIINIAFMNTFGNGQTPDINLAGHCHWSW  80  SEQ ID NO:7
XP_028773281.1  MSSKTQALVLLLSPLLLLSHLSSSQGCPIVTYWGQNVNEGELST-----------------FGNGQTPDINLAGHCYASW  63  SEQ ID NO:8
XP_028773268.1  MASKTQALVLLLWPLLLLSHLSSSQSCPIVTYWGQNVNEGELDAACQTKKYEIINIAFMNTFGNGQTPDINLAGHCSASW  80  SEQ ID NO:9
XP_028773271.1  MASKTQALVLLLWPLLLLSHLSSSQSCPIVTYWGQNVNEGELDAACQTKKYEIINIAFMNTFGNGQTPDINLAGHCHWSS  80  SEQ ID NO:10
XP_028788031.1  MASKPQALVLLLWPLLLLSHLSSSLSCPIVTYWGKNVNEGELDAACQTKKYEIINIAFMNTFGNGQTPDINLAGHCHWSW  80  SEQ ID NO:11
```

FIG. 2B

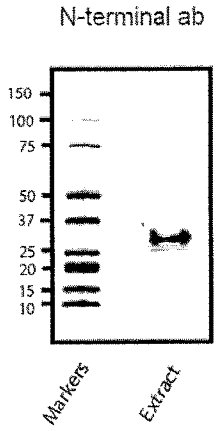

FIG. 2C

```
                                              Signal Sequence
Momordica balsimina - ATGGAATCTCAATTTTGTTCTTCATTTCCATGTTTTATTCTCCTCGTAATTTTCCCTTTTA---TGGGTATTATTCCGAAGCAATAATT 87
Momordica chantaria - ATGGAATCTCAATTTTGTTCTTCATTTCCACGTTTTCTTCTCCTCATAATTCTCGCTTCTATATGGGTTGTTATTCGGAAGC---AATT 87

ACCGGCGGCGGAATTGCGACTTATTGGGGCCAGGACACGAGAGAGGGCCGACTGACCGCCGCCTGCGCCACCGGAAAATTTCAGATCATCAACATAGGGTTCCTCTCTACATT 200
ACCGGCGGCGGAATTGCGACTTACTGGGGCCAGAACACGAGAGAGGGCCGCTGACCGCCGCCTGCGCCACCGGAAAATTTCAGATCATCAACATAGGGTTCCTCTCTACATT 200

CGGCAACGGCCGGCCGCCGCAAGTGAACCTAACGCGCCACTGCAGTCCCATCTCCAACGGTTGCCGGAATGTGAGCGTCGGCGTCCTCAACTGCCGAAACGACGGCGTTAAAG 313
CGGCAACGGCCGGCCGCCGCAAGTGAACCTAACGCGCCACTGCAGTCCCGTCTCCAACGGCTGCCGGAATGTGAGCGTGGCGTCCTCAACTGCCGAAACGATGGCGTTAAAG 313

TCATGCTCTCCATCGGTGGCCCTCAAGGAAGCTACTCCCTCTCCTCCGCCGCCGAAGCCATTGACCTTGCTGACTACATCTGGAACAATTCCTCGGTGGCCCTCCACGTCA 427
TCATGCTCTCCATCGGTGGCCCTCACGGAAGCTACTCCCTCTCCTCCGCCGCCGAAGCCGTTGACCTTGCTGACTACATCTGGAACAATCCTCGGCGGCCCTCCACGTCA 427

CTACGACCCTTCGGTGATGTGCCATTGGACGGGGTAGATTTCAGGATTGAACGACGTCAAGTTCTCCCACTACTACCCTATGGTTGCTCGGCGGCTACACGACTATGGCCGCC 539
CTACGACCGTTCGGTGATGTACCATTGGACGGCGTAGATTTCAGGATTGACCGACGTCAAGTTCTCCCACTACTACCCATGGTTGCTCGGCGGCTACACGACTATGGCCGCC 539

AAGTAACCGTAAAGTGTACCTAACGGCGGCTCCGGCTGCCGTTTTCCAGACAAGTACCTAACAGAATCGCTTCACACTGGACTTTTCGACTATGTTTGGGTTAGATTTTTT 651
AAGTACCGTAAAGTGTACCTAACGGCGGCTCCGGCTGCCGTTTTCCGACAATACCTAACGAATGCTTCACACTGGACTTTTCGACTATGTTTGGGTTAGATTTTTT 651

GACGACGACAATGCCAATATTATTCGGTTAACCCGTCTGGCTTTTGGTGGTCGTGGATGCGGTGGAATATTCAATTCCGGCGAGGAAATTTTACTGGGAATTCCGGCATC 765
GACGACGCAATGCCATATGATTCGGTTAACCCGTCGGGCTTTTGGTGGTCGTGGATGCGGTGGACATTCAATTCCGGCGAGGAAATTTTACTGGGAATTCCGGCATC 765

GAAGAAGCCGGAGATGGGTACGTGGCACCAGAGGTGCTGATAAAGGAAGTGCTGCCCTTCTAAGACGTTACCAATTACGGTGCGTTATGCTTTTCGACTTGTCGAATG 877
GAAGAAGCCGGAGATGGGTACGTGGCACCGGAGGTGCTGATAAAGGAAGTGCTGCCCTTTGTAAGAGTTCACAAGTTAGCGGCGTTATGCTTTTCGACTTGTCGAATG 877

ATGTTCAAACTAACTACAGTTCTATAATTAGCAATAGGGTTTGA 921  SEQ ID NO: 12
ATGTTCAAACTAACTACAGTTCTATAATTAGCAATAGGGTTTGA 921  SEQ ID NO: 16

                                              859/921 Identical (93%)
```

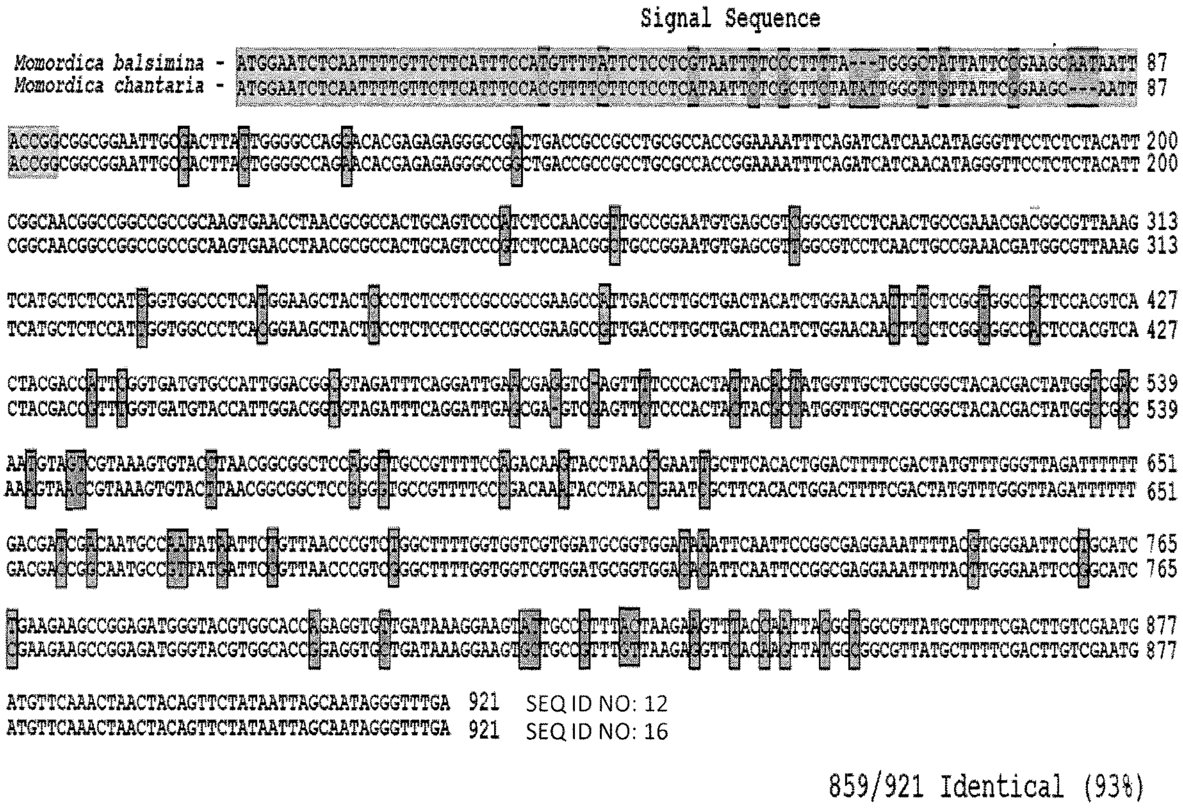

```
                                                                        25
M.balsimina- MESQFCSSFPCFLLVIFPFMGYYSEAITGGGIATYWGQDTREGRLTAACATGKF
M.charantia- MESQFCSSFPRFLLILASLGCYSEAITGGGIATYWGQNTREGRLTAACATGKF

                    45              65   Conserved    85
QIINIGFLSTFGNGRPPQVNLTRHCSPISNGCRNVSVGVLNCRNDGVKVMLSIGGPHGSYSLSSAAEAID
QIINIGFLSTFGNGRPPQVNLTRHCSPVSNGCRNVSVGVLNCRNDGVKVMLSIGGPHGSYFLSSAAEAVD

         105        Conserved  135                    155
LADYIWNNFLGGRSTSLRPFGDVPLDGVDFRIERGQFSHYYTMVARRLHDYGRQCSRKVYLTAAPGCRFP
LADYIWNNFLGGHSTSLRPFGDVPLDGVDFRIERVEFSHYYAMVARRLHDYGRQSNRKVYLTAAPGCRFP

        175                 195                 215              235
DKYLTELHTGLFDYVWVRFFDDRQCQYNSVNPSGFWWSWMRWINSIPARKFYVGIPASEEAGDGYVAPE
DKYLTESLHTGLFDYVWVRFFDDRQCRYDSVNPSGFWWSWMRWHSIPARKFYLGIPASEEAGDGYVAPE

                  255              275
VLIKEVLPFTKKFTNYGGVMLFDLSNDVQTNYSSIISNRV*   SEQ ID NO: 14
VLIKEVLPFVKRFTSYGGVMLFDLSNDVQTNYSSIISNRV*   SEQ ID NO: 17
```

B

GGIATYWGQDTREGRLTAACATGKFQIINIGFLSTFGNGRPPQVNLTRHCSPISNGCRNVSVGVL
NCRNDGVKVMLSIGGPHGSYSLSSAAEAIDLADYIWNNFLGGRSTSLRPFGDVPLDGVDFRIERG
QFSHYYTMVARRLHDYGRQCSRKVYLTAAPGCRFPDKYLTELLHTGLFDYVWVRFFDDRQCQYN
SVNPSGFWWSWMRWINSIPARKFYVGIPASEEAGDGYVAPEVLIKEVLPFTKKFTNYGGVMLFD
LSNDVQTNYSSIISNRV  SEQ ID NO: 15

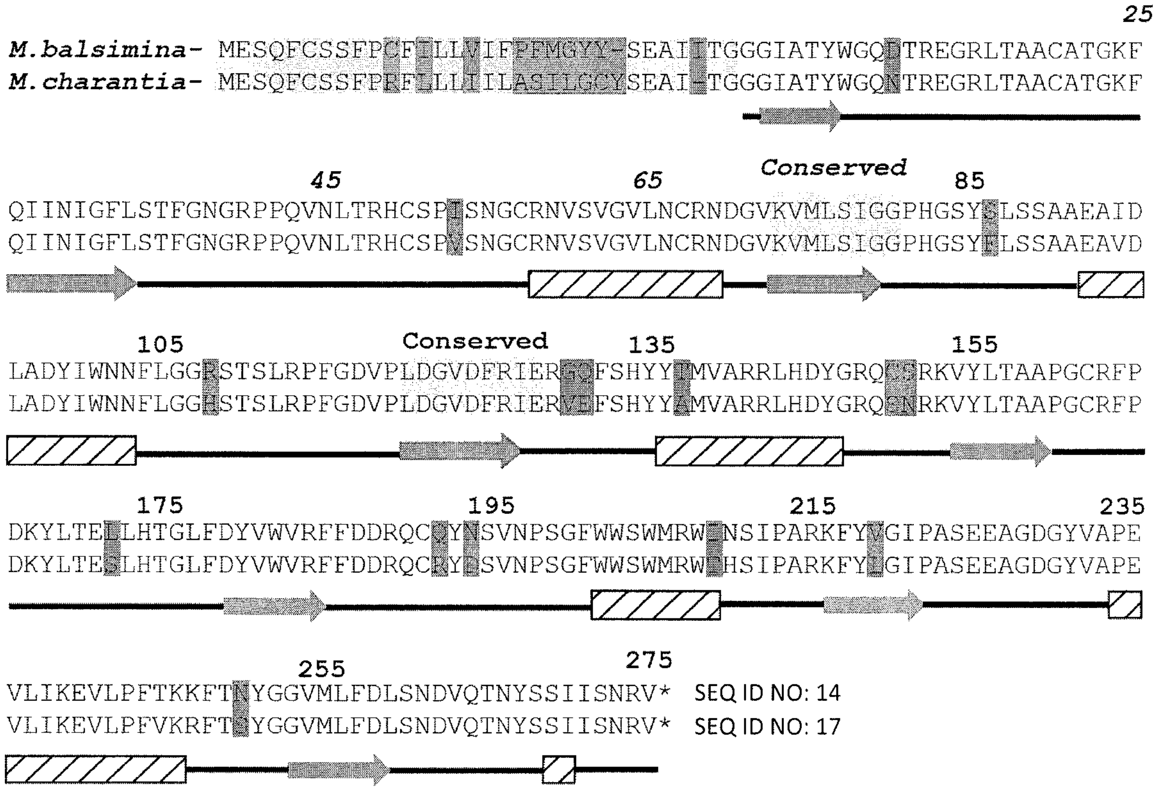

FIG. 8

| | | | | | | |
|---|---|---|---|---|---|---|
| **Momordica balsamina** | 73 | KVMLSLGG | . . . | LDGIDFDIE | 127 | SEQ ID NO: 18 |
| **Momordica charantia** | 73 | KVLLSIGG | . . . | LDGVDFDIE | 127 | SEQ ID NO: 19 |
| **Hevea** | 73 | KVMLSLGG | . . . | LDGIDFDIE | 127 | SEQ ID NO: 20 |
| **Cucumis** | 98 | KVLLSIGG | . . . | LDGVDFDIE | 152 | SEQ ID NO: 21 |
| **Nicotana** | 89 | KTFLSIAG | . . . | FHGLDLDWE | 138 | SEQ ID NO: 22 |
| **Saccharomyces** | 102 | KVLLSLGG | . . . | VDGFDFDIE | 157 | SEQ ID NO: 23 |
| **Alteromonas** | 265 | KILPSIGG | . . . | YDGVDIDWE | 313 | SEQ ID NO: 24 |
| **Bacillus A1** | 158 | KTIISVGG | . . . | FDGVDLDWE | 204 | SEQ ID NO: 25 |
| **Manduca sextaipsum** | 257 | KFMVAVGG | . . . | FDGLDLDWE | 146 | SEQ ID NO: 26 |

FIG. 9

METHODS AND COMPOSITIONS FOR TREATING CORONAVIRUS INFECTIONS

This application is a continuation-in-part application of U.S. patent application Ser. No. 16/996,153, filed on Aug. 18, 2020. The entirety of the aforementioned applications is incorporated herein by reference.

FIELD

The present application generally relates to methods for treating respiratory infections. More particularly, the present application relates to an antiviral composition comprising a plant HEVAR or MOMO30 protein or nucleic acid product therefrom for treatment and prevention of coronavirus infections, such as SARS-CoV-2.

BACKGROUND

The surfaces of host cells and viruses are decorated by complex glycans, which play multifaceted roles in the dynamic interplay between the virus and the host including viral entry into host cell, modulation of proteolytic cleavage of viral proteins, recognition and neutralization of virus by host immune system (Raman, R. et al., Curr. Opin. Struct. Biol., 40: 153-162, 2016). These roles are mediated by specific multivalent interactions between cell surfaces decorated by complex glycans and their cognate protein lectins.

Lectin proteins are sugar-binding proteins that bind specifically and reversibly to carbohydrate groups. They are typically anchored on the surfaces of cells and are found in all groups of living organisms including plants, animals, fungi and bacteria, as well as viruses and mycoplasmas. Depending on their broad sugar-binding specificity, they have been classified as mannose-, galactose-, N-acetylglucosamine-, fucose- and sialic acid-binding lectins, according to the simple sugars that inhibit their carbohydrate-binding properties.

The complex glycans displayed on host cell surfaces typically act as attachment factors, co-receptors or primary receptors that are specifically recognized by viral surface glycoprotein similarly decorated by a variety of glycans. For example, complex glycans terminated by $\alpha$2-3 or $\alpha$2-6-linked sialic acid (N-acetyl neuraminic acid) act as receptors for several different viruses. Linear sulfated glycosaminoglycans such as heparan sulfate act as co-receptors for a variety of viruses, including dengue virus, hepatitis C virus, and foot-and-mouth disease virus. The display of specific glycan motifs on surfaces of different cells and tissues contributes to the host restriction and cell/tissue tropism of viruses.

The complex glycans on the viral surface also play a key role in host immune response to counter the viral infection and play a dual role to enhance antigen presentation and processing for adaptive immune responses. In particular, sites of N-linked glycosylation are often positively selected during evolution of a virus in human hosts to increase glycans on the viral surface so as to present glycans that mimic self-antigens and mask the underlying protein epitope which in turn permits the virus to evade host immune response.

A wide variety of lectins from animals, plants, algae, cyanobacteria and other sources have been shown to possess antiviral activity against a wide variety of viruses, including coronaviruses, human immunodeficiency viruses (HIVs), influenza viruses, herpes simplex viruses, Ebola viruses, and others. See e.g., Mani et al., Virus Res., Apr. 30, 2020, pp. 197989; Akkouh et al., Molecules, 20:648-668, 2015). For example, mannose binding lectin (MBL), a serum protein in humans important in host defenses has been shown to selectively bind to the SARS CoV Spike (S) protein in a SARS-CoV pseudotyped virus and potently inhibit SARS-CoV infection of susceptible cell lines at concentrations below those observed in the serum of healthy individuals (Zhou, Y et al., J Virol., 84(17): 8753-8764, 2010). Mutagenesis indicated that a single N-linked glycosylation site, N330, was critical for the specific interactions between MBL and SARS-S. Id. Exemplary lectins with broad spectrum antiviral activity against multiple viruses include Concanavalin A from jack bean, Griffithsin from red algae, and Cyanovirin-N from cyanobacteria.

The inventor of the present application has recently identified a potential broad spectrum antiviral agent termed MOMO30, which has properties characteristic of lectins. See co-pending U.S. patent application Ser. No. 16/718,994, filed Dec. 18, 2019, which is expressly incorporated by reference herein. In particular, MOMO30 was found to bind HIV-1, simian immunodeficiency virus 1 (SIV-1), Ebola virus, and murine leukemia virus (MuLV).

As of Jun. 3, 2020, the outbreak of SARS-CoV-2 infections, also known as COVID-19, has affected 21,294,845 individuals, caused 761,779 deaths (WHO Situation report-209; Aug. 16, 2020), and has affected the entire world (213 countries/areas/territories). The USA alone reported 5,258,565 infected cases with the highest number of fatalities (n=167,201). Presently, there are virtually no FDA approved antiviral agents showing efficacy for treatment or prevention of coronavirus infections, such as SARS-CoV-2. In view of the outbreak and its toll on human lives, there is a need for prophylactic and therapeutic options for treating coronavirus infections, especially those caused by SARS-CoV-2.

SUMMARY

In one aspect, the present application relates to a method for treating or preventing a viral infection, comprising orally administering to a subject in need thereof a pharmaceutical composition comprising an effective amount of a hevamine A-related (HEVAR) protein which comprises an amino acid sequence at least 90% identical to SEQ ID NO: 15 and at least one pharmaceutically acceptable carrier. In one embodiment, the amino acid sequence is at least 95% identical to SEQ ID NO: 15. In another embodiment, the amino acid sequence comprises the amino acid sequence of SEQ ID NO: 15.

In another aspect, a method for preventing or reducing the severity of the cytokine storm in a SARS-CoV-2 infected patient comprises administering an effective amount of a pharmaceutical composition a pharmaceutical composition comprising an effective amount of a (HEVAR protein which comprises an amino acid sequence at least 90% identical to SEQ ID NO: 15 and at least one pharmaceutically acceptable carrier, where the method results in a reduction of at least 10%, 20%, 50% or 80% in cytokine levels for one or more of IL-6, IL-1$\beta$, IL-2, IL-10, IFN-$\gamma$, TNF-$\alpha$, GM-CSF, or VEGF. In one embodiment, the amino acid sequence is at least 95% identical to SEQ ID NO: 15. In another embodiment, the amino acid sequence comprises the amino acid sequence of SEQ ID NO: 15.

In preferred embodiments, the infection is caused by a Severe Acute Respiratory Syndrome Corona Virus (SARS-CoV), such as SARS-CoV-2, SARS-CoV-1, or Middle East Respiratory Syndrome Coronavirus (MERS-CoV).

In one embodiment, the composition is in a dried form, such as a capsule or tablet. In another embodiment, the composition is in a liquid form. In a particular embodiment, the liquid form comprises an herbal tea.

In another embodiment, the composition comprises a second antiviral agent targeting a viral infection. In certain particular embodiments, the second antiviral agent targets an infection caused by SAR-CoV-2, SARS-CoV-1 or MERS.

In another aspect, a pharmaceutical composition comprises a substantially pure HEVAR protein which comprises an amino acid sequence at least 90% identical to SEQ ID NO: 15; and at least one pharmaceutically acceptable carrier. In one embodiment, the HEVAR protein comprises the amino acid sequence of SEQ ID NO: 15.

In one embodiment, the composition is in a dried form, such as a capsule or tablet. In another embodiment, the composition is in a liquid form. In a particular embodiment, the liquid form comprises an herbal tea.

In one embodiment, the HEVAR protein is prepared by the steps of: (a) drying a plant comprising HEVAR protein; (b) extracting the dried plant in aqueous media; (c) lysing cells from the extracted plant to form a plant cell lysate; and (d) centrifuging the plant cell lysate to remove debris and particulates to form a clarified plant cell lysate; and (e1) passing the plant cell lysate through a molecular weight cut-off filter and collecting the HEVAR-containing retentate, or (e2) purifying the HEVAR protein from the clarified plant cell lysate by immunoaffinity purification using an anti-HEVAR antibody.

In another aspect, the present application provides a composition comprising a nucleic acid having at least 95% or 100% identity to SEQ ID NO: 12 or SEQ ID NO: 13. In another embodiment. In a particular embodiment, the nucleic acid is operatively linked to an expression vector.

In another aspect, the present application provides a cell comprising a nucleic acid, plasmid or expression vector encoding an HEVAR protein.

In another aspect, the present application provides a method for treating or preventing a viral infection, comprising orally administering to a subject in need thereof a pharmaceutical composition comprising: an effective amount of an expression vector operatively linked to a nucleic acid having at least 95% or 100% identity to the nucleotide sequence of SEQ ID NO: 12 or SEQ ID NO: 13; and at least one pharmaceutically acceptable carrier.

In another aspect, the present application relates to a method for treating or preventing a coronavirus (CoV) infection, comprising orally administering to a subject in need thereof a composition comprising an effective amount of a MOMO30 protein prepared by a method includes the steps of: (a) drying plant comprising MOMO30 protein; (b) extracting the dried plant in aqueous media; (c) lysing cells from the extracted plant to form a plant cell lysate; (d) centrifuging the plant cell lysate to remove debris and particulates to form a clarified plant cell lysate; and (e) preparing the MOMO30 protein composition by: (i) passing the clarified plant cell lysate through a molecular weight cut-off filter and collecting the MOMO30-containing retentate; or (ii) purifying the MOMO30 protein from the clarified plant cell lysate by immunoaffinity purification using an anti-MOMO30 antibody. The composition comprising the MOMO30 protein purified therefrom is orally administered to the subject in liquid or dried form.

In certain preferred embodiments, the plant comprising MOMO30 is a member of the *Momordica* genus. In a more particular embodiment, the plant is *Momordica balsamina.*

In some embodiments, the method for preparing the MOMO30 protein composition comprises the step of subjecting the plant extract to immunoaffinity purification prior to administration. In other embodiments, the method includes the step of eluting the MOMO30 retentate in an aqueous buffer to form an aqueous MOMO30 protein composition in solution.

In some embodiments, the MOMO30 protein composition is administered to the subject in a dried form, such as a capsule or tablet. In other embodiments, the MOMO30 protein composition is administered to the subject in liquid form. In certain particular embodiments the MOMO30 protein composition is formulated as an herbal tea for oral administration in liquid form.

In another aspect, a method for preparing a MOMO30 protein composition, includes the steps of: (a) drying a plant comprising MOMO30 protein; (b) extracting the dried plant in aqueous media; (c) lysing cells from the extracted plant to form a plant cell lysate; (d) centrifuging the plant cell lysate to remove debris and particulates to form a clarified plant cell lysate; and (e1) passing the plant cell lysate through a molecular weight cut-off filter and collecting the MOMO30-containing retentate, or (e2) purifying the MOMO30 protein from the clarified plant cell lysate by immunoaffinity purification using an anti-MOMO30 antibody, such that the MOMO30 protein composition formed therefrom is substantially free of plant components less than 10 kDa in size and includes a protein of about 30 kDa in size that is stable after boiling at 100° C. for 20 min, binds CoV S protein and is derived from a MOMO30 protein having a signal peptide comprising the amino acid sequence of SEQ ID NO: 1.

In certain preferred embodiments, the plant comprising MOMO30 protein is a member of the *Momordica* genus. In a more particular embodiment, the plant is *Momordica balsamina.*

In another aspect, the present application provides a pharmaceutical composition containing MOMO30 protein for treating or preventing a coronavirus infection in which the pharmaceutical composition is prepared by a method including the steps of: (a) drying a plant comprising MOMO30 protein; (b) extracting the dried plant in aqueous media; (c) lysing cells from the extracted plant to form a plant cell lysate; (d) centrifuging the plant cell lysate to remove debris and particulates to form a clarified plant cell lysate; (e) preparing a dried MOMO30 protein composition therefrom; (f) adding one or more pharmaceutically acceptable carriers to the dried MOMO30 protein composition, and (g) forming a pharmaceutically acceptable oral composition therefrom in the form of a powder, capsule, tablet, or liquid. The composition resulting therefrom is substantially free of plant components less than 10 kDa in size, and includes a protein of about 30 kDa in size that is stable after boiling at 100° C. for 20 min, binds CoV S protein and is derived from a MOMO30 protein having signal peptide comprising the amino acid sequence of SEQ ID NO: 1.

In certain preferred embodiments, the plant comprising MOMO30 protein is a member of the *Momordica* genus. In a more particular embodiment, the plant is *Momordica balsamina.*

In some embodiments, the clarified plant cell lysate is passed through a 30-50 kDa molecular weight cut-off filter prior to preparing the dried MOMO30 protein composition. In other embodiments, the clarified plant cell lysate is subjected to immunoaffinity purification using an anti-MOMO30 antibody prior to preparing the dried MOMO30 protein composition for oral administration.

In some embodiments, the pharmaceutical composition is administered in the form of a powder. In other embodiments, the pharmaceutical composition is administered in the form of a capsule or tablet. In yet other embodiments, the pharmaceutical composition is administered in the form of a liquid.

In specific embodiments, the composition comprising the MOMO30 or HEVAR protein is about 30 kDa in size and is characterized by one or properties such that the composition is substantially free of plant components less than 10 kDa in size, is stable after boiling at 100° C. for 20 min, binds CoV S protein and comprises the HEVAR amino acid sequence of SEQ ID NO: 15 or is derived from a MOMO30 protein having a signal peptide sequence set forth in SEQ ID NO: 1.

In another aspect, a method for preventing or treating a viral infection comprises administering to a subject in need thereof, a MOMO30 protein, HEVAR protein, MOMO30-encoded nucleic acid or HEVAR-encoded nucleic acid by in vivo or ex vivo gene therapy.

BRIEF DESCRIPTION OF THE DRAWINGS

FIG. 1 shows an exemplary process for producing an aqueous plant extract from dried *Momordica balsamina* leaves for purifying the MOMO30 or HEVAR protein.

FIG. 2A shows the N-terminal sequence of MOMO30 as determined by Edman degradation. FIG. 2B shows the top ten hits when the N-terminal sequence was compared to the NR database by BLAST (light blue). FIG. 2C is a western blot showing detection of a 30 kDa protein from a *M. balsamina* plant extract using a rabbit polyclonal antibody directed against the N-terminal amino acids of the MOMO30 protein in panel A.

FIG. 7 shows the nucleotide sequence of the hevamine-related (HEVAR) coding region aligned with the hevamine A-related nucleotide sequence from *Momordica charantia.*

FIG. 8 panel A shows the amino acid sequence of the HEVAR coding region aligned with the hevamine A-related amino acid sequence from *Momordica charantia*. FIG. 8, panel B shows the amino acid sequence of the mature HEVAR (i.e. secreted) protein.

FIG. 9 shows an alignment of two conserved regions from the HEVAR protein against other hevamine A-related proteins.

Figure 3:
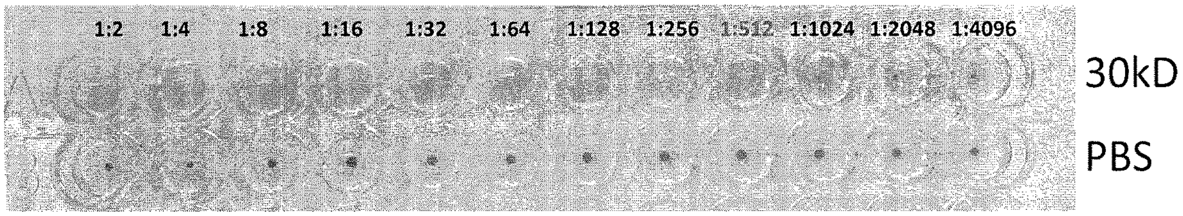
FIG. 3 shows that MOMO30 causes hemagglutination. Purified MOMO30 was tested for its ability to agglutinate sheep red blood cells (RBCs). The stock solution at a dilution of 1:512 was found to cause hemagglutination.

While the present disclosure will now be described in detail, and it is done so in connection with the illustrative embodiments, it is not limited by the particular embodiments illustrated in the figures and the appended claims.

DETAILED DESCRIPTION OF THE INVENTION

The invention and accompanying drawings will now be discussed in reference to the numerals provided therein to enable one skilled in the art to practice the present invention. The skilled artisan will understand, however, that the inventions described below can be practiced without employing these specific details, or that they can be used for purposes other than those described herein. Indeed, they can be modified and can be used in conjunction with products and techniques known to those of skill in the art considering the present disclosure. The drawings and descriptions are intended to be exemplary of various aspects of the invention and are not intended to narrow the scope of the appended claims. Furthermore, it will be appreciated that the drawings may show aspects of the invention in isolation and the elements in one figure may be used in conjunction with elements shown in other figures.

It will be appreciated that reference throughout this specification to aspects, features, advantages, or similar language does not imply that all the aspects and advantages may be realized with the present invention should be or are in any single embodiment of the invention. Rather, language referring to the aspects and advantages is understood to mean that a specific aspect, feature, advantage, or characteristic described in connection with an embodiment is included in at least one embodiment of the present invention. Thus, discussion of the aspects and advantages, and similar language, throughout this specification may, but do not necessarily, refer to the same embodiment.

The described aspects, features, advantages, and characteristics of the invention may be combined in any suitable manner in one or more further embodiments. Furthermore, one skilled in the relevant art will recognize that the invention may be practiced without one or more of the specific aspects or advantages of a particular embodiment. In other instances, additional aspects, features, and advantages may be recognized and claimed in certain embodiments that may not be present in all embodiments of the invention.

Unless otherwise defined, all technical and scientific terms used herein have the same meaning as commonly understood by one of ordinary skill in the art to which this application belongs. One of skill in the art will recognize many techniques and materials similar or equivalent to those described here, which could be used in the practice of the aspects and embodiments of the present application. The described aspects and embodiments of the application are not limited to the methods and materials described.

As used in this specification and the appended claims, the singular forms “a,” “an” and “the” include plural referents unless the content clearly dictates otherwise.

Ranges may be expressed herein as from “about” one particular value, and/or to “about” another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to "the value," greater than or equal to the value" and possible ranges between values are also disclosed, as appropriately understood by the skilled artisan. For example, if the value "10" is disclosed the "less than or equal to 10" as well as "greater than or equal to 10" is also disclosed.

As used herein, the term "preprotein" is used with reference to a predicted amino acid sequence including an N-terminal signal peptide, which is cleaved off during protein processing resulting in a secreted biologically active mature protein as described herein.

As used herein, the term "MOMO30 protein" is used with reference to a 30 kDa plant protein from *Momordica balsamina* that is stable after boiling or autoclaving at 120° C. for 20 min, and exhibits mannose-sensitive binding to cell surface proteins. Additionally, a MOMO30 protein or MOMO30 homolog comprises an amino acid sequence that is 100%, 99.9%, 99.5%, 99%, 95%, 94%, 93%, 92%, 91%, or 90 identical (including any percent homology range therefrom) to the MOMO30 amino acid sequence of SEQ ID NO: 1. Additional embodiments related to MOMO30 and applicable to the present disclosure are described in co-pending U.S. patent application Ser. Nos. 16/718,994 and 16/996,153, the disclosures of which are incorporated by reference in their entirety.

As used herein, the term "HEVAR protein" refers to a hevamine A-related protein from *Momordica balsamina*. Additionally a "HEVAR protein" or "HEVAR homolog" comprises an amino acid sequence that is 100%, 99.9%, 99.5%, 99%, 95%, 94%, 93%, 92%, 91%, or 90% identical (including any percent homology range therefrom) to the HEVAR preprotein amino acid sequence of SEQ ID NO: 14 or the HEVAR mature amino acid sequence of SEQ ID NO: 15.

The phrase "cytokine storm" refers to an excessively activated cytokine cascade or hypercytokinemia, i.e., an excessive or uncontrolled release of proinflammatory cytokines, which can be associated with a wide variety of infectious and noninfectious diseases or disorders.

The phrase "antiviral agent" refers to a small molecule, protein or antibody that can inhibit the progression of coronavirus infections or induce or mediate the death (e.g., necrosis or apoptosis) of coronavirus-infected cells in a subject (e.g., a human).

The terms "treat" and "treatment" refer to the amelioration of one or more symptoms associated with a viral infection; prevention or delay of the onset of one or more symptoms of a viral infection; and/or lessening of the severity or frequency of one or more symptoms of the infection.

The phrases "effective amount" "therapeutically effective", "pharmacologically effective amount" are used interchangeably to mean the amount(s) of one or more antiviral agents needed to provide a threshold level of active antagonist agents in the bloodstream or in the target tissue. The precise amount will depend upon numerous factors, e.g., the particular active agent, the components and physical characteristics of the composition, intended patient population, patient considerations, and the like, and can readily be determined by one skilled in the art, including based upon the information provided herein or otherwise available in the relevant literature.

The phrases "pharmaceutical composition comprises" and "pharmaceutical composition comprising" should be interpreted such that the "comprises" or "comprising" components are included in a single pharmaceutical composition or in one or more independent pharmaceutical compositions.

The terms, "improve", "increase" or "reduce", as used in this context, indicate values or parameters relative to a baseline measurement, such as a measurement in the same individual prior to initiation of the treatment described herein, or a measurement in a control individual (or multiple control individuals) in the absence of the treatment described herein.

The term "control individual" is an individual who is not afflicted with the same viral infection as the individual being treated, who is about the same age as the individual being treated (to ensure that the stages of the disease in the treated individual and the control individual(s) are comparable). The individual (also referred to as "patient" or "subject") being treated may be a fetus, infant, child, adolescent, or adult human.

Methods of Treatment

The present application provides a method for preventing or treating viral infections, particularly those caused by respiratory viruses, such as coronaviruses and influenza viruses.

In one aspect, the application relates to a method for treating or preventing a viral infection, comprising orally administering to a subject in need thereof a pharmaceutical composition comprising: an effective amount of hevamine A-related (HEVAR) protein which comprises an amino acid sequence at least 90% identical to SEQ ID NO: 15; and at least one pharmaceutically acceptable carrier. In one embodiment, the amino acid sequence is at least 95% identical to SEQ ID NO: 15. In another embodiment, the amino acid sequence comprises the amino acid sequence of SEQ ID NO: 15. The amino acid sequence of SEQ ID NO: 15 corresponds to the mature (secreted) HEVAR protein from *Momordica balsamina*. Exemplary symptoms include high fever, coughing, shortness of breath, inflammation (redness and swelling), hypercytokinemia, hypoxemia, low lung capacity and volume, lung fibrosis, fatigue, sore throat, muscle pains, headache, runny nose, and nausea.

In a preferred embodiment, the virus is Severe Acute Respiratory Syndrome Coronavirus-2 (SARS-CoV-2). In other preferred embodiments, the virus is Severe Acute Respiratory Syndrome Coronavirus-1 (SARS-CoV-1) or Middle East Respiratory Syndrome Coronavirus (MERS-CoV).

In another aspect, a pharmaceutical composition comprises an HEVAR protein which comprises an amino acid sequence at least 90%, 95% or 99% identical to SEQ ID NO: 15; and at least one pharmaceutically acceptable carrier. In one embodiment, the HEVAR protein comprises the amino acid sequence of SEQ ID NO: 15.

In one embodiment, the HEVAR-containing composition is in a dried form, such as a capsule or tablet. In another embodiment, the composition is in a liquid form. In a particular embodiment, the liquid form comprises an herbal tea.

In one embodiment, the HEVAR protein is prepared by the steps of: (a) drying a plant comprising HEVAR protein; (b) extracting the dried plant in aqueous media; (c) lysing cells from the extracted plant to form a plant cell lysate; and (d) centrifuging the plant cell lysate to remove debris and particulates to form a clarified plant cell lysate; and (e1) passing the plant cell lysate through a molecular weight cut-off filter and collecting the HEVAR-containing retentate, or (e2) purifying the HEVAR protein from the clarified plant cell lysate by immunoaffinity purification using an anti-HEVAR antibody.

In another aspect, the present application provides a composition comprising a nucleic acid having at least 90%, 95%, 99% or 100% identity to SEQ ID NO: 12.

In another aspect, the present application provides a cell comprising a plasmid or expression vector comprising a nucleic acid having at least 90%, 95% or 100% identity to the nucleotide sequence of SEQ ID NO: 12.

In another aspect, the present application provides a method for treating or preventing a viral infection, comprising orally administering to a subject in need thereof a pharmaceutical composition comprising: an effective amount of an expression vector operatively linked to a nucleic acid having at least 95% identity to the nucleotide sequence of SEQ ID NO: 12; and at least one pharmaceutically acceptable carrier.

In preferred embodiments, the virus is SARS-CoV-2, SARS-CoV-1 or MERS.

A major objective in treating coronavirus patients, particularly SARS-CoV-2 infected patients, is to reduce viral loads and prevent or reduce the severity of the cytokine storm and its potentially lethal effects. A number of cytokines with anti-inflammatory properties are responsible for the cytokine storm, such as IL-10 and transforming growth factor β (TGF-β). Each cytokine acts on a different part of the inflammatory response. For example, products of the Th2 immune response suppress the Th1 immune response and vice versa. By resolving the associated inflammation, one can minimize collateral damage to surrounding cells, with little or no long-term damage to the patient.

Accordingly, another aspect of the present application relates to a method for preventing or reducing the severity of the cytokine storm in a SARS-CoV-2 infected patient comprises administering an effective amount of a pharmaceutical composition a pharmaceutical composition comprising an effective amount of a hevamine A-related (HEVAR) protein which comprises an amino acid sequence at least 90% identical to SEQ ID NO: 15 and at least one pharmaceutically acceptable carrier, where the method results in a reduction of at least 10%, 20%, 50% or 80% in cytokine levels for one or more of IL-6, IL-1β, IL-2, IL-10, IFN-γ, TNF-α, GM-CSF, or VEGF. In one embodiment, the amino acid sequence is at least 95% identical to SEQ ID NO: 15. In another embodiment, the amino acid sequence comprises SEQ ID NO: 15. To inhibit or reduce the coronavirus-associated cytokine storm, the pharmaceutical compositions of the present application may be administered alone or in combination with one or more antiviral agents, including those described below, including cytokine antagonists to the cytokines described herein.

In another aspect, a method for preventing or treating a viral infection comprises administering to a subject in need thereof a pharmaceutical composition comprising MOMO30 protein, a MOMO30 extract, MOMO30-containing combination formulation or a MOMO30-encoded nucleic acid according to the present application to reduce the symptoms associated with the infection or cure the subject of the disease. In preferred embodiments, the virus is SARS-CoV-2, SARS-CoV-1 or MERS-CoV.

The MOMO30 product is derived from *Momordica balsamina* and is characterized by multiple properties, including: (1) a size of about 30 kDa; (2) solubility in aqueous solutions; (3) high heat resistance or high stability as reflected in no appreciable loss of activity following autoclaving at 120° C. for 30 min; (4) exhibiting mannose sensitive binding; (5) insensitive to digestion with trypsin following denaturation in 8M urea and overnight and partially sensitive to subtilisin after overnight treatment; (6) having hemagglutinin activity; (7) capable of activating and stimulating T cell proliferation; (8) having chitinase activity; (9) having an amino terminal amino acid sequence of SEQ ID NO: 1, which is at least 93% identical to a hevamine A-related protein from *Prosopis alba*. In addition, the MOMO30 and HEVAR proteins are believed to bind CoV S protein and exhibit mannose-sensitive binding to CoV S protein (data not shown).

In certain embodiments, the MOMO30 or HEVAR protein has an amino acid sequence that is 90%, 95%, 96%, 97%, 98%, 99% or 100% identical to SEQ ID NO: 1. In one embodiment, the MOMO30 protein is isolated from a plant of the *Momordica* genus, a species therefrom, such as *Momordica balsamina*, or any homolog thereof.

Without wishing to be bound by theory, MOMO30 and HEVAR are believed to be a carbohydrate binding agents with two distinct modes of action: (1) inhibition of virus by blocking entry into cells; (2) selecting for mutations in a viral surface protein that allow the host to produce a broadly neutralizing antibody response. MOMO30 and HEVAR are believed to inhibit virus binding via its binding to carbohydrates, particularly cell surface mannose residues. The more carbohydrates on a surface protein, such as CoV S protein (i.e., spike protein), the more targets will be available for inhibiting virus. Under such pressure, the presence of MOMO30 or HEVAR selects for viruses with fewer glycosyl groups. Fewer glycosyl groups on the CoV S protein allows more epitopes to be exposed and allows the production of neutralizing antibodies. As a consequence, patients treated with HEVAR or MOMO30 in the short-term exhibit the production of a broadly neutralizing antibody response. The same patients should also develop a broadly neutralizing antibody response to control their infection in the long term.

The compositions and methods of the present application may be applied to any coronavirus in the Orthocoronavirinae family, including but not limited to those described herein. The genetically diverse Orthocoronavirinae family is divided into four genera (alpha, beta, gamma, and delta coronaviruses). Human CoVs are limited to the alpha and beta subgroups. Exemplary human CoVs include severe acute respiratory syndrome coronavirus-2 (SARS-CoV-2), severe acute respiratory syndrome coronavirus (SARS-CoV), Middle East respiratory syndrome coronavirus (MERS-CoV), HCoV-229E, HCoV-OC43, HCoV-NL63, and HCoV-HKU1.

Before the advent of human SARS CoV-2 (also known as COVID-19), human coronaviruses were believed to cause 10% of all upper and lower respiratory tract infections, which typically present with common-cold like symptoms, but were known to cause more severe disease in young children, as well as people with underlying respiratory conditions (i.e. asthma, COPD) and the elderly.

Zoonotic CoVs have a natural predilection for emergence into new host species giving rise to new diseases most recently exemplified in humans by severe acute respiratory syndrome coronavirus 2 (SARS-CoV-2), severe acute respiratory syndrome coronavirus (SARS-CoV), and Middle East respiratory syndrome coronavirus (MERS-CoV) (de Wit et al., 2016). Interestingly, all known human CoVs are thought to have emerged as zoonoses from wild or domestic animals.

Nonlimiting examples of subgroup 1a alphacoronaviruses and their GenBank Accession Nos. include FCov.FIPV.79.1146.VR.2202 (NV_007025), transmissible gastroenteritis virus (TGEV) (NC_002306; Q811789.2; DQ811786.2; DQ811788.1; DQ811785.1; X52157.1; AJ011482.1; KC962433.1; AJ271965.2; JQ693060.1; KC609371.1; JQ693060.1; JQ693059.1; JQ693058.1; JQ693057.1; JQ693052.1; JQ693051.1; JQ693050.1); porcine reproductive and respiratory syndrome virus (PRRSV) (NC_001961.1; DQ811787), as well as any subtype, clade or sub-clade thereof, including any other subgroup 1a coronavirus now known (e.g., as can be found in the GenBank® Database) or later identified in the GenBank® Database.

Nonlimiting examples of a subgroup 1b alphacoronaviruses and their GenBank Accession Nos. include HCoV.NL63.Amsterdam.I (NC_005831), BtCoV.HKU2.HK.298.2006 (EF203066), BtCoV.HKU2.HK.33.2006 (EF203067), BtCoV.HKU2.HK.46.2006 (EF203065), BtCoV.HKU2.GD.430.2006 (EF203064), BtCoV.1A.AFCD62 (NC_010437), BtCoV.1B.AFCD307 (NC_010436), BtCov.HKU8.AFCD77 (NC_010438), BtCoV.512.2005 (DQ648858); porcine epidemic diarrhea viruses (NC_003436, DQ355224.1, DQ355223.1, DQ355221.1, JN601062.1, JN601061.1, JN601060.1, JN601059.1, JN601058.1, JN601057.1, JN601056.1, JN601055.1, JN601054.1, JN601053.1, JN601052.1, JN400902.1, JN547395.1, FJ687473.1, FJ687472.1, FJ687471.1, FJ687470.1, FJ687469.1, FJ687468.1, FJ687467.1, FJ687466.1, FJ687465.1, FJ687464.1, FJ687463.1, FJ687462.1, FJ687461.1, FJ687460.1, FJ687459.1, FJ687458.1, FJ687457.1, FJ687456.1, FJ687455.1, FJ687454.1, FJ687453.1, FJ687452.1, FJ687451.1, FJ687450.1, FJ687449.1, AF500215.1, KF476061.1, KF476060.1, KF476059.1, KF476058.1, KF476057.1, KF476056.1, KF476055.1, KF476054.1, KF476053.1, KF476052.1, KF476051.1, KF476050.1, KF476049.1, KF476048.1, KF177258.1, KF177257.1, KF177256.1, KF177255.1), HCoV.229E (NC_002645), as well as any subtype, clade or sub-clade thereof, including any other subgroup 1b coronavirus now known (e.g., as can be found in the GenBank© Database) or later identified in the GenBank© Database.

Nonlimiting examples of subgroup 2a betacoronaviruses and their GenBank Accession Nos. include HCoV.HKU1.C.N5 (DQ339101), MHV.A59 (NC_001846), PHEV.VW572 (NC_007732), HCoV.OC43.ATCC.VR.759 (NC_005147), bovine enteric coronavirus (BCoV.ENT) (NC_003045), as well as any subtype, clade or sub-clade thereof, including any other subgroup 2a coronavirus now known (e.g., as can be found in the GenBank© Database) or later identified in the GenBank© Database.

Nonlimiting examples of subgroup 2b betacoronaviruses and their GenBank Accession Nos. include human SARS CoV-2 isolates, such as Wuhan-Hu-1 (NC_045512.2) and any CoV-2 isolates comprising a genomic sequence set forth in GenBank Accession Nos., such as MT079851.1, MT470137.1, MT121215.1, MT438728.1, MT470115.1, MT358641.1, MT449678.1, MT438742.1, LC529905.1, MT438756.1, MT438751.1, MT460090.1, MT449643.1, MT385425.1, MT019529.1, MT449638.1, MT374105.1, MT449644.1, MT385421.1, MT365031.1, MT385424.1, MT334529.1, MT466071.1, MT461669.1, MT449639.1, MT415321.1, MT385430.1, MT135041.1, MT470179.1, MT470167.1, MT470143.1, MT365029.1, MT114413.1, MT192772.1, MT135043.1, MT049951.1; human SARS CoV-1 isolates, such as SARS CoV.A022 (AY686863), SARSCoV.CUHK-W1 (AY278554), SARSCoV.GD01 (AY278489), SARSCoV.HC.SZ.61.03 (AY515512), SARS-CoV.SZ16 (AY304488), SARSCoV.Urbani (AY278741), SARSCoV.civet010 (AY572035), SARSCoV.MA.15 (DQ497008); bat SARS CoV isolates, such as BtSARS.HKU3.1 (DQ022305), BtSARS.HKU3.2 (DQ084199), BtSARS.HKU3.3 (DQ084200), BtSARS.Rm1 (DQ412043), BtCoV.279.2005 (DQ648857), BtSARS.Rf1 (DQ412042), BtCoV.273.2005 (DQ648856), BtSARS.Rp3 (DQ071615),), as well as any subtype, clade or sub-clade thereof, including any other subgroup 2b coronavirus now known (e.g., as can be found in the GenBank® Database) or later identified in the GenBank® Database.

Nonlimiting examples of subgroup 2c betacoronaviruses and their GenBank Accession Nos. include Middle East respiratory syndrome coronavirus (MERS) isolates, such as Riyadh 22012 (KF600652.1), Al-Hasa_18_2013 (KF600651.1), Al-Hasa_17_2013 (KF600647.1), Al-Hasa_15_2013 (KF600645.1), Al-Hasa_16_2013 (KF600644.1), Al-Hasa_21_2013 (KF600634), Al-Hasa 19_2013 (KF600632), Buraidah_1_2013 (KF600630.1), Hafr-Al-Batin_1_2013 (KF600628.1), Al-Hasa_12_2013 (KF600627.1), Bisha.ltoreq.1_2012 (KF600620.1), Riyadh_3_2013 (KF600613.1), Riyadh_1_2012 (KF600612.1), Al-Hasa_3_2013 (KF186565.1), Al-Hasa_1_2013 (KF186567.1), Al-Hasa_2_2013 (KF186566.1), Al-Hasa_4_2013 (KF186564.1); Betacoronavirus England 1-N1 (NC_019843), SA-N1 (KC667074); human betacoronavirus 2c Jordan-N3/2012 (KC776174.1); human betacoronavirus 2c EMC/2012, (JX869059.2); any bat coronavirus subgroup 2c isolate, such as bat coronavirus Taper/CII_KSA_287/Bisha/Saudi Arabia (KF493885.1), bat coronavirus Rhhar/CII_KSA 003/Bisha/Saudi Arabia/2013 (KF493888.1), bat coronavirus Pikuh/CII_KSA_001/Riyadh/Saudi Arabia/2013 (KF493887.1), bat coronavirus Rhhar/CII_KSA 002/Bisha/Saudi Arabia/2013 (KF493886.1), bat coronavirus Rhhar/CII_KSA_004/Bisha/Saudi Arabia/2013 (KF493884.1), bat coronavirus BtCoV.HKU4.2 (EF065506), bat coronavirus BtCoV.HKU4.1 (NC_009019), bat coronavirus BtCoV.HKU4.3 (EF065507), bat coronavirus BtCoV.HKU4.4 (EF065508), bat coronavirus BtCoV133.2005 (NC_008315), bat coronavirus BtCoV.HKU5.5 (EF065512), bat coronavirus BtCoV.HKU5.1 (NC_009020), bat coronavirus BtCoV.HKU5.2 (EF065510), bat coronavirus BtCoV.HKU5.3 (EF065511), and bat coronavirus HKU5 isolate (KC522089.1); any additional subgroup 2c, such as KF192507.1, KF600656.1, KF600655.1, KF600654.1, KF600649.1, KF600648.1, KF600646.1, KF600643.1, KF600642.1, KF600640.1, KF600639.1, KF600638.1, KF600637.1, KF600636.1, KF600635.1, KF600631.1, KF600626.1, KF600625.1, KF600624.1, KF600623.1, KF600622.1, KF600621.1, KF600619.1, KF600618.1, KF600616.1, KF600615.1, KF600614.1, KF600641.1, KF600633.1, KF600629.1, KF600617.1, KC869678.2, KC522088.1, KC522087.1, KC522086.1, KC522085.1, KC522084.1, KC522083.1, KC522082.1, KC522081.1, KC522080.1, KC522079.1, KC522078.1, KC522077.1, KC522076.1, KC522075.1, KC522104.1, KC522104.1, KC522103.1, KC522102.1, KC522101.1, KC522100.1, KC522099.1, KC522098.1, KC522097.1, KC522096.1, KC522095.1, KC522094.1, KC522093.1, KC522092.1, KC522091.1, KC522090.1, KC522119.1, KC522118.1, KC522117.1, KC522116.1, KC522115.1, KC522114.1, KC522113.1, KC522112.1, KC522111.1, KC522110.1, KC522109.1, KC522108.1, KC522107.1, KC522106.1, KC522105.1); *Pipistrellus* bat coronavirus HKU4 isolates (KC522048.1, KC522047.1, KC522046.1, KC522045.1, KC522044.1, KC522043.1, KC522042.1, KC522041.1, KC522040.1, KC522039.1, KC522038.1, KC522037.1, KC522036.1, KC522048.1, KC522047.1, KC522046.1, KC522045.1, KC522044.1, KC522043.1, KC522042.1, KC522041.1, KC522040.1, KC522039.1, KC522038.1, KC522037.1, KC522036.1, KC522061.1, KC522060.1, KC522059.1, KC522058.1, KC522057.1, KC522056.1, KC522055.1, KC522054.1, KC522053.1, KC522052.1, KC522051.1, KC522050.1, KC522049.1, KC522074.1, KC522073.1, KC522072.1, KC522071.1, KC522070.1, KC522069.1, KC522068.1, KC522067.1, KC522066.1, KC522065.1, KC522064.1, KC522063.1, KC522062.1), as well as any subtype, clade or sub-clade thereof, including any other subgroup 2c coronavirus now known (e.g., as can be found in the GenBank® Database) or later identified in the GenBank® Database.

Nonlimiting examples of subgroup 2d betacoronaviruses and their GenBank Accession Nos. include BtCoV.HKU9.2 (EF065514), BtCoV.HKU9.1 (NC_009021), BtCoV.HkU9.3 (EF065515), BtCoV.HKU9.4 (EF065516), as well as any subtype, clade or sub-clade thereof, including any other subgroup 2d coronavirus now known (e.g., as can be found in the GenBank© Database) or later identified in the GenBank© Database.

Nonlimiting examples of subgroup 3 gammacoronaviruses include IBV.Beaudette.IBV.p65 (DQ001339) or any other subgroup 3 coronavirus now known (e.g., as can be found in the GenBank® Database) or later identified in the GenBank® Database.

A coronavirus defined by any of the isolates or genomic sequences in the aforementioned subgroups 1a, 1b, 2a, 2b, 2c, 2d and 3 can be targeted for prophylactic or therapeutic use in accordance with the methods and compositions of the present application.

The methods of the present application may be also be used to prevent or treat other viral infections that are inhibited by the HEVAR protein, MOMO30 protein, HEVAR-encoded expression vector or a MOMO30-encoded expression vector. Viruses for treatment include enveloped RNA and DNA viruses. In certain preferred embodiments, the virus includes one or more surface proteins containing mannose residues.

In addition to coronaviruses, exemplary RNA viruses for prophylactic or therapeutic treatment include retroviruses (e.g., HIV-1, HIV-2, HTLV-I, HTLV-II); bunyaviruses (e.g., Rift Valley fever virus, Crimean-Congo hemorrhagic fever virus); filoviruses (e.g., Ebola virus, Marburg virus); flaviviruses (e.g., Hepatitis C virus, West Nile virus, Dengue fever virus, Zika virus, yellow fever virus, tick-borne encephalitis virus, Saint Louis encephalitis virus, GB virus C); enteroviruses (Types A to L, including coxsackieviruses (Types A to C), echoviruses, rhinoviruses (Types A to C), poliovirus); orthomyxoviruses (e.g., influenza Types A, -B, -C, -D, including A subtypes H1N1, H5N1, H3N2); paramyxoviruses (e.g., rubulavirus (mumps), rubeola virus (measles), respiratory syncytial virus, Newcastle disease, parainfluenza); parvoviruses (e.g., parvovirus B19 virus); rhabdoviruses (e.g., Rabies virus); arenaviruses (e.g., lymphocytic choriomeningitis virus and several Lassa fever viruses, including Guanarito virus, Junin virus, Lassa virus, Lujo virus, Machupo virus, Sabia virus, Whitewater Arroyo virus); alphaviruses (e.g., Venezuelan equine encephalitis virus, eastern equine encephalitis virus; western equine encephalitis virus); Hepatitis A virus; Hepatitis D virus; Hepatitis E virus; as well as any type, subtype, clade or sub-clade thereof.

In other preferred embodiments, the RNA virus for prevention or treatment is a respiratory virus, such as influenza Type A virus. Influenza A viruses are divided into subtypes on the basis of two proteins on the surface of the virus, hemagglutinin (HA) and neuraminidase (NA). There are 18 known HA subtypes and 11 known NA subtypes. Many different combinations of HA and NA proteins are possible. For example, an "H7N2 virus" designates an influenza A virus subtype that has an HA7 protein and an NA2 protein. Similarly, an "H5N1" virus has an HA5 protein and an NA1 protein. Type A influenza viruses that may be targeted for prophylactic and/or therapeutic use according to the methods and compositions of the present application include a variety of sub-types, such as H1N1, H1N2, H3N2, H5N1, H5N2, H5N3, H5N4, H5N5, H5N6, H5N7, H5N8, and H5N9, H7N1, H7N2, H7N3, H7N4, H7N5, H7N6, H7N7, H7N8, H7N9, H9N1, H9N2, H9N3, H9N4, H9N5, H9N6, H9N7, H9N8, H9N9, H17N10 and H18N11).

In one embodiment, a method for treating or preventing an influenza Type A virus infection, comprises orally administering to a subject in need thereof a composition comprising: an effective amount of a HEVAR protein which comprises an amino acid sequence that is at least 90% identical to SEQ ID NO: 15; and at least one pharmaceutically acceptable carrier.

Exemplary DNA viruses for prophylactic or therapeutic treatment include herpesviruses (e.g., HSV-1, HSV-2, EBV, VZV, HCMV-1, HHV-6, HHV-7, HHV-8), papillomaviruses (e.g., human papilloma virus (HPV) Types 1, 2, 4, 6, 11, 16, 18, 26, 30, 31, 33, 34, 35, 39, 40, 41, 42, 43, 44, 45, 51, 52, 54, 55, 56, 57, 58, 59, 61, 62, 64, 67, 68, 69, 70); poxviruses (e.g., smallpox virus), hepadnaviruses (Hepatitis B virus); anelloviruses (e.g., transfusion transmitted virus or torque teno virus (TTV)); as well as any type, subtype, clade or sub-clade thereof.

Route and Dose of Antiviral Product Administration

The antiviral MOMO30 or HEVAR product of the present application may be administered orally, intrathecally, intraarterially, intravenously, intradermally, subcutaneously, transdermally (topically) or transmucosally. An antiviral composition may be administered by any route, including oral, rectal, pulmonary, sublingual, and parenteral administration. Parenteral administration includes, for example, intraperitoneal, intravenous, intramuscular, intraarterial, intravesical (e.g., to the bladder), intradermal, transdennal, topical, or subcutaneous administration.

As a general proposition, the therapeutically effective amount of an antiviral MOMO30 or HEVAR protein administered will be in a weight range of about 1 ng/kg body weight/day to about 100 mg/kg body weight/day whether by one or more administrations. In more particular embodiments, the antiviral MOMO30 protein or HEVAR protein is administered in weight range from about 1 ng/kg body weight/day to about 1 μg/kg body weight/day, 1 ng/kg body weight/day to about 100 ng/kg body weight/day, 1 ng/kg body weight/day to about 10 ng/kg body weight/day, 10 ng/kg body weight/day to about 1 μg/kg body weight/day, 10 ng/kg body weight/day to about 100 ng/kg body weight/day, 100 ng/kg body weight/day to about 1 μg/kg body weight/day, 100 ng/kg body weight/day to about 10 μg/kg body weight/day, 1 μg/kg body weight/day to about 10 μg/kg body weight/day, 1 μg/kg body weight/day to about 100 μg/kg body weight/day, 10 μg/kg body weight/day to about 100

μg/kg body weight/day, 10 μg/kg body weight/day to about 1 mg/kg body weight/day, 100 μg/kg body weight/day to about 10 mg/kg body weight/day, 1 mg/kg body weight/day to about 100 mg/kg body weight/day and 10 mg/kg body weight/day to about 100 mg/kg body weight/day.

In other embodiments, an antiviral MOMO30 or HEVAR protein is administered at a dosage range of 1 ng-10 ng per injection, 10 ng-100 ng per injection, 100 ng-1 μg per injection, 1 μg-10 μg per injection, 10 μg-100 μg per injection, 100 μg-1 mg per injection, 1 mg-10 mg per injection, 10 mg-100 mg per injection, and 100 mg-1000 mg per injection. The MOMO30 protein, HEVAR protein, or formulation thereof, may be injected once daily, twice daily, three times daily, and/or every 2, 3, 4, 5, 6 or 7 days. In addition, the MOMO30 or HEVAR protein or formulation thereof may be administered over a period of one month, two months, six months, 12 months, 2 years, 5 years, 10 years, 20 years, or more.

In other embodiments, the antiviral MOMO30 protein, HEVAR protein, or formulation thereof may be administered in a range from about 1 ng/kg to about 100 mg/kg. In more particular embodiments, the antiviral MOMO30 protein, HEVAR protein, or formulation thereof may be administered in a range from about 1 ng/kg to about 10 ng/kg, about 10 ng/kg to about 100 ng/kg, about 100 ng/kg to about 1 μg/kg, about 1 μg/kg to about 10 μg/kg, about 10 μg/kg to about 100 μg/kg, about 100 μg/kg to about 1 mg/kg, about 1 mg/kg to about 10 mg/kg, about 10 mg/kg to about 100 mg/kg, about 0.5 mg/kg to about 30 mg/kg, and about 1 mg/kg to about 15 mg/kg.

In other particular embodiments, the amount of the antiviral MOMO30 or HEVAR protein is administered is, or is about, 0.0006, 0.001, 0.003, 0.006, 0.01, 0.03, 0.06, 0.1, 0.3, 0.6, 1, 3, 6, 10, 30, 60, 100, 300, 600 and 1000 mg/day.

Concentrations or amounts of MOMO30 or HEVAR protein may be determined using anti-MOMO30 or anti-HEVAR antibodies as further described herein below. The specific dose of antiviral MOMO30 or HEVAR product may be determined based on the particular circumstances of the individual patient including the size, weight, age and sex of the patient, the nature and stage of the disease, the aggressiveness of the disease, and the route of administration of the antiviral composition.

In certain embodiments, an antiviral MOMO30 product, HEVAR product, MOMO30-containing formulation or HEVAR-containing formulation may be administered at least once per day, typically once, twice, three times or four times per day with the doses given at equal intervals throughout the day and night in order to maintain a constant presence of the drug in order to provide sufficient antiviral activity. However, a skilled artisan will appreciate that a treatment schedule can be optimized for any given patient, and that administration of compound may occur less frequently than once per day.

In other embodiments, an antiviral MOMO30 product, HEVAR product, MOMO30-containing formulation or HEVAR-containing formulation of the present application may be administered in combination with other antiviral agents. Exemplary antiviral agents for treating coronavirus infections include viral polymerase inhibitors, such as Remdesivir, GS-441524, Faviravir, EIDD-2801, EIDD-2901, EIDD-1931, Ribavirin, 6-azauridine; convalescent plasma; neutralizing mAbs or mAbs inhibiting coronavirus attachment or entry, such as REGN10933, REGN10987, LY3819253, AZD7442, BRII-196, CT-P59, JS016, SCTA01, STI-1499, TY027, 47D11; anti-IL6 monoclonal antibodies, such as Tocilizumab; protease inhibitors targeting $M^{pro}$, such as Lopinavir, Ritonavir, Dipyridamole, and Danoprevir; Ivermectin; Saracatinib; protease inhibitors targeting TMPRSS2, such as Camostat, Nafomastat, and Nafomastat mesylate; S-protein targeted drugs, such as Arbidol (umifenovir) and Hydroxychloroquine; cytokines, such as interferons-α, -β, -λ, Dexamethasone, Anakinra, Hydrocortisone, Azithromycin, Ulinastatin and Ciclesonide; Janus kinase inhibitors, such as Ruxolitinib and Baricitinib; AXL kinases inhibitors, such as Bemcentinib; Dihydroorotate dehydrogenase (DHODH) inhibitors, such as PTC299; recombinant ACE2; HR2P-EK1C4, IPB03 and other lipopeptide fusion inhibitors described herein above; Fluvoxamine; Apilomod; Ciclesonide; Tetrahydroquinoline oxocarbazate; GC373; Vitamin D; $Zn^{2+}$; and combinations thereof. When used in such combinations, each of the antiviral MOMO30 or HEVAR product may be co-administered with the antiviral agent(s) simultaneously, separately, by the same or different routes, and/or at different times during treatment.

The treatment may be carried out for as long a period as necessary, i.e., until the infection is cleared or no longer a threat to the host. In some cases, the treatment may be continued indefinitely while the disease state persists, although discontinuation might be indicated if the antiviral compositions no longer produce a beneficial effect. In one embodiment, the treatment is carried out for 6 months and then discontinued. The treating physician can determine whether to increase, decrease, or interrupt treatment based on a patient's response, including evaluation of immune responses, viral loads etc.

MOMO30 and HEVAR Products for Use in the Present Application

In another aspect, the present application contemplates plant homologs or variants of MOMO30 or HEVAR having about 80% to about 100% nucleotide or amino acid sequence identity to a complete MOMO30 or HEVAR nucleotide or amino acid sequence, including any and all whole numbers within, as well as any subranges within, wherein the lower number can be any whole number between 810% and 99% and the upper number can be any whole number between 82% and 100%.

In some embodiments, the MOMO30 or HEVAR protein (or homolog thereof) is encoded by a plant species of the *Momordica* genus. Exemplary *Momordica* species include, but are not limited to, *M. aculeata, M. acuminate, M. acutangula, M. adoensis, M. affinis, M. amaniana, M. angolensis, M. angulate, M. angustisepala, M. anigosantha, M. anthelmintica, M. argillicola, M. aspera, M. auriculata, M. balsamina, M. bequaertii, M. bicolor, M. boivinii, M. brachybotrys, M. bracteata, M. brevispinosa, M. bricchettii, M. cabraei, M. calantha, M. calcarata, M. camerounensis, M. cardiospermoides, M. carinata, M. casea, M. charantia, M. chinensis, M. cirrhiflora, M. cissoides, M. clarkeana, M clematidea, M. cochinchinensis, M. cochinchinensis, M. cogniauxiana, M. cordata, M. cordatifolia, M. coriacea, M corymbifera, M. covel, M. crinocarpa, M. cucullata, M. cylindrica, M. cymbalaria, M. dasycarpa, M. denticulata, M. denudata, M. dictyosperma, M. dioica, M. diplotrimera, M. dissecta, M. eberhardtii, M. echinata, M. echinocarpa, M. ecirrhata, M. elastica, M. elaterium, M. elegans, M. enneaphylla, M. erinocarpa, M. fasciculata, M. foetida, M. friesiorum, M. gabonii, M. garipensis, M. garriepensis, M. gilgiana, M. glabra, M. glauca, M. gracilis, M. grandibracteata, M. grosvenorii, M. guttata, M. hamiltoniana, M. hamiltoniana, M. henriquesii, M. heterophylla, M. heyneana, M. hispida, M. huberi, M. humilis, M. hystrix, M. indica, M. involucrata, M. jagorana, M. jeffreyana, M. kirkii, M. lambertiana, M. lanata, M. laotica, M. laurentii,*

*M. leiocarpa, M. littorea, M. luffa, M. luffa, M. macrantha, M. macropetala, M. macrophylla, M. macropoda, M. macrosperma, M. maculata, M. mannii, M. marlothii, M. martinicensis, M. meloniflora, M microphylla, M. missionis, M. mixta, M. monadelpha, M. morkorra, M. mossambica, M. multicrenulata, M. multiflora, M. muricata, M. obtusisepala, M. officinarum, M operculata, M. ovata, M. paina, M. palmata E, M. papillosa, M. parvifolia, M. pauciflora, M. pedata, M. pedisecta, M peteri, M. procera, M. pterocarpa, M. punctata, M. purgans, M. pycnantha, M. quinquefida, M. quinqueloba, M. racemiflora, M. racemosa, M. renigera, M. repens, M reticulata, M. rostrata, M. rotunda, M. roxburghiana, M. rumphii, M runssorica, M. rutshuruensis, M. sahyadrica, M. sativa, M. schimperiana, M. schinzii, M. schliebenii, M. senegalensis, M. sessilifolia, M. sicyoides, M. silvatica, M. sinensis, M. somalensis, M. sphaeroidea, M. spicata, M spinosa, M. stefaninii, M. subangulata, M. surculata, M. suringarii, M. thollonii, M. tonkinensis, M. trifolia, M. trifoliata, M. trilobata, M. tuberosa, M. tubiflora, M. tubulosa, M. umbellata, M. verticillata, M. vogelii, M. wallichii, M. welwitschii, M. wildemaniana, M. zeylanica*, and *M. zeylanica*. In some embodiments, the MOMO30 or HEVAR protein may be obtained from any of the foregoing *Momordica* leaf extracts, fruit extracts, root extracts, bark extracts, seed extracts and/or any flower thereof.

In certain preferred embodiments, the MOMO30 or HEVAR protein is obtained from *Momordica balsamina* leaf extracts. In other embodiments, the MOMO30 or HEVAR protein is obtained from *Momordica balsamina* fruit extracts, root extracts, bark extracts, seed extracts and/or any flower thereof. In yet other embodiments, the MOMO30 or HEVAR protein is prepared from cells transformed with an expression vector encoding *M. balsamina* MOMO30 or HEVAR, or any other MOMO30 or HEVAR plant source.

In other embodiments, the MOMO30 or HEVAR protein (or homolog thereof) is encoded by a plant species of the *Prosopis* genus. Exemplary *Prosopis* species include, but are not limited to, *P. abbreviata, P. affinis, P. african, P. alba, P. chilensis, P. cineraria, P. farcta, P. fiebrigii, P. flexuosa, P. glandulosa, P. hassleri, P. julflora, P. laevigata, P. koelziana, P. kuntzei, P. nigra, P. pallida, P. pubescens, P. reptans, P. rojasiana, P. ruscifolia, P. spicigera, P. strombuhifera, P. tamarugo*, and *P. velutina*. In some embodiments, the MOMO30 protein may be obtained from any of the foregoing *Prosopis* leaf extracts, fruit extracts, root extracts, bark extracts, seed extracts and/or any flower thereof.

In some embodiments, the MOMO30 or HEVAR protein is 100%, 99.9%, 99.5%, 99%, 95%, 94%, 93%, 92%, 91%, 90%, 89%, 88%, 87%, 86%, 85%, 84%, 83%, 82%, 81%, or 80% identical to the amino acid sequence of the *Momordica balsamina* MOMO30 or HEVAR protein, including any range therefrom.

In some embodiments, the MOMO 30 or HEVAR protein is a variant containing one or more mutations relative to the wild-type sequence. "Variants" include protein sequences having one or more amino acid additions, deletions, stop positions, or substitutions, as compared to a wild-type protein. An amino acid substitution can be a conservative or a non-conservative substitution. Variants of MOMO30 or HEVAR proteins can include those having one or more conservative amino acid substitutions. A "conservative substitution" or "conservative amino acid substitution" involves a substitution found in one of the following conservative substitutions groups: Group 1: Alanine (Ala; A), Glycine (Gly; G), Serine (Ser; S), Threonine (Thr; T); Group 2: Aspartic acid (Asp; D), Glutamic acid (Glu; E); Group 3: Asparagine (Asn; N), Glutamine (Gln; Q); Group 4: Arginine (Arg; R), Lysine (Lys; K), Histidine (His; H); Group 5: Isoleucine (Ile; I), Leucine (Leu; L), Methionine (Met; M), Valine (Val; V); and Group 6: Phenylalanine (Phe; F), Tyrosine (Tyr; Y), Tryptophan (Trp; W).

Additionally, amino acids can be grouped into conservative substitution groups by similar function, chemical structure, or composition (e.g., acidic, basic, aliphatic, aromatic, or sulfur-containing). For example, an aliphatic grouping may include, for purposes of substitution, G, A, V, L, and I. Other groups including amino acids that are considered conservative substitutions for one another include: sulfur-containing: M and C; acidic: D, E, N, and Q; small aliphatic, nonpolar or slightly polar residues: A, S, T, P, and G; polar, negatively charged residues and their amides: D, N, E, and Q; polar, positively charged residues: H, R, and K; large aliphatic, nonpolar residues: M, L, I, V, and C; and large aromatic residues: F, Y, and W.

Non-conservative substitutions include those that significantly affect: the structure of the peptide backbone in the area of the alteration (e.g., the alpha-helical or beta-sheet structure); the charge or hydrophobicity of the molecule at the target site; or the bulk of the side chain. Non-conservative substitutions which in general are expected to produce the greatest changes in a protein's properties may include those in which e.g., (i) a hydrophilic residue (e.g., S or T) is substituted for (or by) a hydrophobic residue (e.g. L, I, F, V, or A); (ii) a C or P is substituted for (or by) any other residue; (iii) a residue having an electropositive side chain (e.g. K, R, or H) is substituted for (or by) an electronegative residue (e.g., Q or D); or (iv) a residue having a bulky side chain (e.g., F) that is substituted for (or by) one not having a bulky side chain, (e.g., G).

MOMO30 and HEVAR mutants may be generated by random mutagenesis or site-directed mutagenesis using methods known to those of ordinary skill in the art with or without selection methodologies employing binding assays, functional assays, apoptosis assays and the like.

In some embodiments, the present application provides a nucleic acid encoding a MOMO30 or HEVAR protein of the present application. In some embodiments, the MOMO30- or HEVAR-encoded nucleic acid is 99.9%, 99%, 95%, 94%, 93%, 92%, 91% or 90% identical to a *Momordica balsamina* MOMO30 or HEVAR cDNA. In certain particular embodiments, the MOMO30- or HEVAR-encoded nucleic acid includes a codon-optimized MOMO30 or HEVAR nucleic acid encoding the 30 kDa *M. balsamina* MOMO30 or HEVAR protein.

In some embodiments, the present application provides an expression vector comprising a MOMO30- or HEVAR-encoded nucleic acid.

In other embodiments, the present application provides a host cell transformed with a MOMO30- or HEVAR-encoded nucleic acid or a MOMO30- or HEVAR-encoded expression vector.

The HEVAR protein, MOMO30 protein, HEVAR-encoded nucleic acid or MOMO30-encoded nucleic acid may be administered with a pharmaceutically acceptable carrier, alone or in combination with a suitable adjuvant, or it may be administered as a plant extract alone or in combination with other nutritional supplements, plant extracts, plant components or secondary antiviral agents.

In another aspect, the present application provides an extract comprising a MOMO30 or HEVAR protein. The extract may prepared for oral administration or parenteral administration (e.g., intravenous (IV), intramuscular (IM), subcutaneous (SC or SQ), transdermal (TD)). The extract may be in dried form or it may be in aqueous solution, with or without one or more pharmaceutically acceptable carriers. In one embodiment, the extract is an herbal extract from a natural plant source, such as *M. balsamina*. In another embodiment, the extract is a cell extract from bacterial, fungal, plant, insect, or animal cells transformed with a MOMO30 or HEVAR expression vector to express the protein. The transformed cells may be stably transformed or they may be transiently transformed. The extract may be prepared and its composition may be modified in accordance with any of the methods of preparation outlined below or known to those of ordinary skill in the art.

In some embodiments, the MOMO30 protein, HEVAR protein, MOMO30-containing extract or HEVAR-containing extract is combined with one or more nutritional supplements selected from the group consisting of minerals and metals, vitamins, salts, amino acids, fatty acids, proteins, and other pharmaceutically acceptable excipients. The nutritional supplement may be included with the MOMO30 protein, HEVAR protein, MOMO30-containing extract or HEVAR-containing extract as in a MOMO30 or HEVAR formulation, or it may be separately administered therewith. Exemplary supplements include vitamin A, vitamin B1, vitamin B2, vitamin B5, vitamin B6, vitamin B12, vitamin C, magnesium citrate, vitamin E, vitamin D3, calcium, zinc citrate, selenium, manganese gluconate, copper gluconate, copper gluconate, Coenzyme Q, biotin, folate, acetyl-L-carnitine, chromium polynicotinate, citrus bioflavinoids, glucosamine sulfate, boron sulfate, and whey protein. Exemplary fatty acids may be selected from the group consisting of linoleic acid (LA), gamma linoleic acid (GLA), eicosapentaneoic acid (EPA), docosapentaneoic Acid (DPA), docosahexaenoic acid (DHA), and D-alpha-tocopherol.

Alternatively, or in addition, in some embodiments, the MOMO30 protein, HEVAR protein, MOMO30-containing extract or HEVAR-containing extract may be combined with one or more MOMO30 or HEVAR homologs, plant extracts and/or or plant substances to form a MOMO30 or HEVAR combination formulation. Exemplary plant extracts, MOMO30 homologs and/or HEVAR homologs in such combination formulations may be obtained from one or more members selected from the group consisting of *Acacia arabia, Afromomum melegueta, Agrimonia eupatoria, Ajuga decumbens, Allium cepa, Allium sativum, Aloe vera, Alternanthera philoxeroides* or *sessiles, Ammi maius, Andographis paniculata, Apium graveolens, Apium leptophyllum, Arachis hypogaea, Arctium lappa, Artemesia Judaica, Amebia euhcroma, Asparagus racemosus, Astragalus spinosus, Astragalus lentingosis swainsonine, Azadirachta indica, Balanites aegyptiaca, Bauhinia rufescens, Bersama tysoniana, Blumea alata, Brucea antidysenterica, Buchenavia capita, Butyrospermum parkii, Bryonia cretica* ssp. *Dioica, Bryonia angustifolia, Calotropis procera, Camellia theifera, Camellia sinensis, Casia sieberiana, Catha edulis. Cedrela toona, Chrysanthemum morifolium, Clausena anisata, Clivia miniata, Cochlospermum planchonii, Coffea arabica, Cola nitida, Combretum glutinosum, Combretum micranthum, Coptis chinesis, Coptis teetoides, Coptis japonica, Coraria nepalensis, Coriandrum sativum, Cryptolepis sanguinolenta, Curcuma longa, Cyperus articulatus, Cyperus domestus, Cyperus rigidifolius, Datura metel syn alba, Daucus carota, Diospyros mespiliformis, Echinacea angustiflora* and *purpurea, Echinacea simulata, Echinacea pallida, Entada abyssinica, Epimedium grandiflorum, Epimedium sagittatum, Epimedium sinense, Epilobium angustifolium, Erigeron Canadensis, Eugenia* or *Syzigium claviflorum, Euphorbia hirta, Faidherbia albida, Fagara xanthox, Ficus iteophylla, Ficus platphylla, Foeniculum vulgarel, Garcinia afzelii, Garcinia epundata, Gardenia coronaria, Gaultheria trichophylla, Glycine max, Glycyrrhiza labra, Gossypium herbaceum, Guiera senegalensis, Heracleum sphondylium, Hypericum perforatum, Hypericum japonicum, Hyssopus officinalis, Jasminum officinale, Khaya senegalensis, Lippia javanica, Lithospermum erythrorhizon, Lonicera japonica, Lophira lanceolate, Luffa, Lycopus europaeus, Magnolia officinalis, Mallotus repandus, Mallotus philippinesis, Matricaria chamomil, Matricaria recutitia, Melissa parviflora, Melissa officinalis, Momordica* species, including *Momordica balsamina, Momordica charantia* and others; *Morinda lucida, Narcissus tazetta, Narcissus pseudonarcissus, Ocimum gratissimum, Oenthera rosea, Paeonia spec., Papaver somniferum, Parkia biglobosa, Perilla frutescens, Persea Americana, Phyllanthus niruri, Pinus koraicenis, Pinus parviflora, Piper nirgum, Plumeria rubra, Polyantha suberosa, Prosopis* sp., *including P. africana* and others; *Prunus africans, Prunella vulgaris, Prunus bakariensis, Prunus amygdalus, Psoralea corylifolia, Randia dunatorum, Raphanus sativus, Rheum palmatum, Rhus coriaria, Rhus chinesis, Ricinus communis, Rosmarinus officinalis, Salic mucronata, Salvia miltiorhiza* and *officinalis, Salvadora persica, Sambucus ebulus, Saussurea lappa, Scilla griffithii, Scutellaria baicalensis baiealein, Sedum sediforme, Senecio scandens, Senecio aereus, Senna alata, Silybum marianum, Skimmia laureola, Solarium niporum, Swertia franchetiana, Tamarindus indica, Terminalia alata, Terminalia catappa, Terminalia chebula, Terminalia glaucescens, Thula occidentalis, Trapalaponica spec., Trichosanthes dioica, Trichosanthes kirilowii, Urtica dioica, Viola yeodensis, Vitellaria paradoxa, Voacanga africana, Woodfordia fruticosa, Woodwardia* spec., *Zanoxylum nitidum, Zanthoxylum zanthoxyloides*, and *Ziziphus mauritania*, including powder or extract from leaf, bark, seed, root, and/or flower therefrom.

In one embodiment, the MOMO30 or HEVAR combination formulation includes one or more plant extracts selected from the group consisting of *Momordica balsamina, Aframomum melegueta, Cyperus domestus, Ficus iteophylla* and *Tamarindus indica*. In another embodiment, the MOMO30 or HEVAR combination formulation includes one or more plant extracts selected from the group consisting of *Momordica balsamina, Aframomum melegueta, Cyperus articulatus, Ficus iteophylla* and *Tamarindus indica*. In another embodiment, the MOMO30 or HEVAR combination formulation includes one more plant extracts selected from the group consisting of *Momordica balsamina, Aframomum melegueta* and *Cyperus articulatus*. In a more particular embodiment, the MOMO30 or HEVAR combination formulation includes a leaf extract from *Momordica balsamina*, a seed extract from *Aframomum melegueta* and/or a root extract from *Cyperus articulatus*.

Exemplary plant-derived substances include lentinan, a polysaccharide isolated from the fruit body of shiitake mushroom (*Lentinula edodes* mycelium) and various ribosome inactivating proteins (RIPs) from *M. balsamina* and *Trichosanthis kirilowii*, such as Momordin I and Momordin II, as well as ribosome inactivating proteins from any of the foregoing plant extracts. It is believed that the addition of the aforementioned nutritional supplements and/or plant-based substances may be further increase the prophylactic and/or therapeutic efficacy of the MOMO30 or HEVAR protein, especially in patients infected with a CoV or any of the other viral infections described herein below.

Another aspect of the application is a method of preparing a MOMO30- or HEVAR-containing plant extract, including but not limited to plants of the *Mormordica* genus, such as

*Momordica balsamina*. In one embodiment, the method includes one or more steps including: harvesting the plants; drying the plants; extracting the dried plants in water or aqueous media; collecting the plant cells by centrifugation; lysing or disrupting the plant cell membranes by physical or chemical means; centrifuging the plant cell lysate to remove debris and particulates; filtering the clarified plant cell lysates by e.g., running the lysate through a molecular weight cutoff (MWCO) filter (e.g., Amicon 30 kDa or 50 kDa); eluting the semi-purified extract from the retentate; drying the semi-purified extract or resuspending the semi-purified extract in buffer for further analysis, purification and/or storage. The MOMO30 protein may be further purified from the plant extract by immunoaffinity chromatography and other conventional methodologies known to those of skill in the art.

In a particular embodiment, a method for preparing a partially purified MOMO30- or HEVAR-containing plant extract comprises the steps of: (a) forming an aqueous plant extract from one or more dried plant leaves comprising a MOMO30 and/or HEVAR protein; (b) lysing the plant cells; (c) centrifuging the aqueous plant extract to remove debris and particulates; (d) retaining the aqueous supernatant; (e) filtering the aqueous supernatant through a MW cutoff filter and/or subjecting the supernatant to immunoaffinity purification; and (f) eluting MOMO30 or HEVAR into buffer for storage and/or use. In certain embodiments, the MOMO30 or HEVAR protein may be dried for storage or resuspended in an appropriate buffer for further use or storage following e.g., quantification of MOMO30 or HEVAR yield and/or characterization of MOMO30 or HEVAR purity. In practice, the extracts are quite stable and have been stored freeze dried for years without significant loss of anti-viral activity.

MOMO30- or HEVAR containing cell extracts, as well as purified MOMO30 or HEVAR proteins may be characterized by HPLC and/or tested for binding and/or functional activities via binding assays, infectivity assays and the like. In some embodiments, the MOMO30- or HEVAR-containing plant extract or purified MOMO30 or HEVAR protein preparation may be evaluated for coronavirus binding activity using commercially available coronavirus reagents, cell lines and/or inhibitor screening assay kits. As further described below, the reagents and kits for these assays may utilize a variety of SARS-CoV-2 S protein-, SARS-CoV-2 S1 subunit (receptor binding domain, RBD) protein-, and/or ACE2 protein reagents, which may be His-tagged, Fc-tagged, Avi-tagged, or biotin-labeled in order to facilitate detection of binding on microtiter plates and the like using suitable colorimetric, chemoluminescent substrates (BPS Bioscience, San Diego, Calif.).

In one embodiment, MOMO30- or HEVAR containing plant extract or purified MOMO30 or HEVAR protein is evaluated for functional activity in an in vitro plaque reduction assay using SARS-CoV-2 infected cells as further described below.

In another embodiment, a MOMO30- or HEVAR containing plant extract or purified MOMO30 or HEVAR protein is evaluated for its ability to inhibit infection by a lentivirus operably linked to a luciferase reporter that is pseudotyped with a CoV Spike (S) protein, such as SARS-CoV-2 S protein, in ACE2-expressing cells. A "bald" or non-pseudotyped lentivirus control containing the luciferase reporter alone can be used as a negative control. These lentivirus vectors, as well as a lentivirus expressing ACE2 can be obtained from BPS Bioscience, San Diego, Calif., BPS #s 79942, 79943 and 79944).

In certain preferred embodiments, the plant leaves comprising MOMO30 or HEVAR protein are obtained from members of the *Momordica* genus. In a more particular embodiment, the plant leaves are obtained from the *Momordica balsamina* plant.

An antiviral MOMO30 or HEVAR protein of the present application can be chemically synthesized or produced from cells transiently or stably transformed with polynucleotide expression vectors operatively linked to a MOMO30 or HEVAR gene using recombinant DNA technologies well known to those skilled in the art. Polynucleotide expression vectors can be designed to facilitate preparative expression levels in many different cell hosts, including bacteria, yeast, insect cells, and mammalian cells.

In some microorganisms, such as wild type *E. coli*, the periplasm constitutes an oxidizing environment, whereas the cytoplasm is a reducing environment. Accordingly, expression in the *E. coli* periplasm may enable the production of peptides containing interchain or intrachain disulfide bonds that might be otherwise reduced in cytoplasm, where it may be toxic to the cell. Some prokaryotic organisms have endogenous, intracellular oxidizing environments and can normally accommodate formation of protein disulfide bonds inside the cell. Accordingly, the fusion protein may be periplasmically expressed using an operably linked periplasmic signal sequence at the 5'end of the corresponding nucleic acid expression construct.

The MOMO30 or HEVAR protein or nucleic acid therefrom may be fused to other protein domains, including binding tags conferring additional biochemical properties, targeting properties, antiviral properties etc. When fused to another protein domain in an expression vector, the MOMO30 or HEVAR encoded nucleic acid may be further engineered to include a cleavage recognition site for proteolytic cleavage of one or more peptide domains from one another. The cleavage recognition sequence can be cleaved by a suitable protease, such as Kex2p or furin, at one or more defined residues.

Where the cleavage recognition site is positioned adjacent to a protein domain, proteolytic cleavage in a transduced cell can liberate one or more antiviral domains from one another so that the antiviral products can function independently of one another according to their designated microbial cell surface target or microbial intracellular target.

For example, when positioned in or adjacent to a spacer region adjacent to the MOMO30 or HEVAR gene product, the expressed protein can be directly cleaved when introduced into a microbial cell bearing the corresponding protease. In one embodiment, the proteolytic recognition site is a Kex2p-sensitive proteolytic cleavage site. In another embodiment, the proteolytic recognition site is the furin proteolytic cleavage site, which is sensitive to cleavage by the enzyme, furin.

An expression construct can further include a native or non-native N-terminal signal peptide region to facilitate entry of the encoded antiviral MOMO30 or HEVAR protein into the secretory pathway following gene transfer into eukaryotic cells near a site of infection.

Expression Vectors

In certain embodiments, an expression vector encoding the antiviral MOMO30 or HEVAR protein of the present application is directly administered to a patient to express an antiviral MOMO30 or HEVAR protein in vivo. In certain particular embodiments, a recombinant polynucleotide operatively linked to suitable regulatory elements for expression of a MOMO30 or HEVAR protein is codon optimized for expression in a selected prokaryotic or eukaryotic host cell, such as a mammalian, plant or insect cell. To facilitate replication and expression, the polynucleotide can be incorporated into a vector, such as a prokaryotic or a eukaryotic expression vector. Suitable non-viral expression vectors include, but are not limited to, plasmid expression vector or a bacteriophage vectors. Suitable viral vectors include, but are not limited to, adeno-associated viral (AAV) vectors, retroviral vectors, lentiviral vectors, adenoviral vectors, herpes viral vectors, and alphavirus vectors. The viral vector can also be an astrovirus, coronavirus, orthomyxovirus, papovavirus, paramyxovirus, parvovirus, picornavirus, poxvirus, togavirus viral vector.

The term "in vivo expression vector" refers to a non-viral or viral vector that comprises a polynucleotide encoding an antiviral MOMO30 or HEVAR protein of the present application in a form suitable for expression of the polynucleotide in a host cell. The expression vectors include one or more regulatory sequences, selected on the basis of the host cells to be used for expression, and operably linked to the polynucleotide sequence to be expressed. It will be appreciated by those skilled in the art that the design of the expression vector can depend on such factors as the choice of the host cell to be transformed, the level of expression of protein desired, and the like. The expression vectors can be introduced into host cells to produce an antiviral MOMO30 or HEVAR protein of the present application.

As used herein, the term "control sequences" or "regulatory sequences" refers to DNA sequences necessary for the expression of an operably linked coding sequence in a particular host organism. The term "control/regulatory sequence" is intended to include promoters, enhancers and other expression control elements (e.g., polyadenylation signals). Control/regulatory sequences include those which direct constitutive expression of a nucleotide sequence in many types of host cells and those which direct expression of the nucleotide sequence only in certain host cells (e.g., tissue-specific regulatory sequences). An expression vector may be designed to facilitate expression of an antiviral MOMO30 or HEVAR protein-encoding polynucleotide in one or more cell types. Tissue-specific regulatory elements may be used to restrict expression to a particular cell type.

A nucleic acid sequence is "operably linked" to another nucleic acid sequence when the former is placed into a functional relationship with the latter. For example, a DNA for a presequence or secretory leader peptide is operably linked to DNA for a protein if it is expressed as a preprotein that participates in the secretion of the protein; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, synthetic oligonucleotide adaptors or linkers are used in accordance with conventional practice.

Delivery of antiviral MOMO30 or HEVAR protein-encoding expression vectors can be achieved by infection (for viral vectors), transfection (for non-viral vectors) and other methods well known to one skilled in the art. Examples of other delivery methods and media include, polycationic condensed DNA linked or unlinked to killed viruses, ligand linked DNA, liposomes, eukaryotic cell delivery vehicles cells, deposition of photopolymerized hydrogel materials, handheld gene transfer particle gun, ionizing radiation, nucleic charge neutralization or fusion with cell membranes. Particle mediated gene transfer may also be employed.

Plasmid DNA expression vectors can be utilized for non-viral gene transfer, either by direct injection of naked DNA or by encapsulating an antiviral MOMO30 or HEVAR protein-encoding polynucleotide in a liposome, microparticle, microcapsule, virus-like particle, or erythrocyte ghost. Such compositions can be further linked by chemical conjugation to, for example, microbial translocation domains and/or targeting domains to facilitate targeted delivery and/or entry of nucleic acids into the nucleus of desired cells to promote gene expression. In addition, plasmid vectors may be incubated with synthetic gene transfer molecules such as polymeric DNA-binding cations like polylysine, protamine, and albumin, and linked to cell targeting ligands such as asialoorosomucoid, insulin, galactose, lactose or transferrin. Naked DNA may also be employed. Uptake efficiency of naked DNA may be improved using biodegradable latex beads. Such delivery may be improved further by treating the beads to increase hydrophobicity and thereby facilitate disruption of the endosome and release of the DNA into the cytoplasm.

As used herein, the term "promoter" is to be taken in its broadest context and includes transcriptional regulatory elements (TREs) from genomic genes or chimeric TREs therefrom, including the TATA box or initiator element for accurate transcription initiation, with or without additional TREs (i.e., upstream activating sequences, transcription factor binding sites, enhancers and silencers) which regulate activation or repression of genes operably linked thereto in response to developmental and/or external stimuli and trans-acting regulatory proteins or nucleic acids. The promoter may be constitutively active or it may be active in one or more tissues or cell types in a developmentally regulated manner. A promoter may contain a genomic fragment or it may contain a chimera of one or more TREs combined together.

Examples of such promoters include: the immediate early promoter of CMV, LTR or SV40 promoter, polyhedron promoter of baculovirus, *E. coli* lac or trp promoter, phage T7 and lambda PL promoter and other promoters known to control expression of genes in prokaryotic or eukaryotic cells or their viruses. The expression vector typically also contains a ribosome binding site for translation initiation and a transcription terminator. The vector optionally includes appropriate sequences for amplifying expression. In addition, the expression vectors optionally comprise one or more selectable marker genes to provide a phenotypic trait for selection of transformed host cells, such as dihydrofolate reductase or neomycin resistance for eukaryotic cell culture or such as tetracycline or ampicillin resistance in *E. coli.*

The expression vector can also include additional expression elements, for example, to improve the efficiency of translation. These signals can include, e.g., an ATG initiation codon and adjacent sequences. In some cases, for example, a translation initiation codon and associated sequence elements are inserted into the appropriate expression vector simultaneously with the polynucleotide sequence of interest (e.g., a native start codon). In such cases, additional translational control signals are not required. However, in cases where only a protein coding sequence or a portion thereof, is inserted, exogenous translational control signals, including an ATG initiation codon is provided for expression of an antiviral MOMO30 or HEVAR protein. The initiation codon is placed in the correct reading frame to ensure translation of the polynucleotide sequence of interest. Exogenous transcriptional elements and initiation codons can be of various origins, both natural and synthetic. If desired, the efficiency of expression can be further increased by the inclusion of enhancers appropriate to the cell system in use (Scharf et al. (1994) Results Probl Cell Differ 20:125-62; Bitter et al. (1987) Methods in Enzymol 153:516-544).

Expression vectors carrying an antiviral MOMO30- or HEVAR-encoding nucleic acid can be introduced into host cells by any of a variety of well-known procedures, such as electroporation, liposome mediated transfection, calcium phosphate precipitation, infection, transfection and the like, depending on the selection of vectors and host cells.

Host cells that contain antiviral MOMO30 or HEVAR protein-encoding nucleic acids are, thus, also a feature of this disclosure. Favorable host cells include prokaryotic (i.e., bacterial) host cells, such as *E. coli*, as well as numerous eukaryotic host cells, including plant (e.g., tobacco), fungal (e.g., yeast, such as *Saccharomyces cerevisiae* and *Picchia pastoris*) cells, insect cells, and mammalian cells (such as CHO cells). Recombinant antiviral MOMO30- or HEVAR-encoding nucleic acids are introduced (e.g., transduced, transformed or transfected) into host cells, for example, via a vector, such as an expression vector. As described above, the vector is most typically a plasmid, but such vectors can also be, for example, a viral particle, a phage, etc. Examples of appropriate expression hosts include: bacterial cells, such as *E. coli, Streptomyces* and *Salmonella typhimurium*; fungal cells, such as *Saccharomyces cerevisiae, Pichia pastoris* and *Neurospora crassa*; insect cells such as *Drosophila* and *Spodoptera frugiperda*; mammalian cells such as 3T3, COS, CHO, BHK, HEK 293 or Bowes melanoma; plant cells, including algae cells, etc.

The host cells can be cultured in conventional nutrient media modified as appropriate for activating promoters, selecting transformants or amplifying the inserted polynucleotide sequences. The culture conditions, such as temperature, pH and the like, are typically those previously used with the host cell selected for expression and will be apparent to those skilled in the art.

In bacterial systems, a number of expression vectors can be selected depending upon the use intended for the expressed product. For example, when large quantities of a protein or fragments thereof are needed for the production of antibodies, vectors which direct high level expression of fusion proteins that are readily purified are favorably employed. Such vectors include, but are not limited to, multifunctional *E. coli* cloning and expression vectors such as BLUESCRIPT (Stratagene), in which the coding sequence of interest, e.g., a polynucleotide of the invention as described above, can be ligated into the vector in-frame with e.g., sequences for the amino-terminal translation initiating methionine and the subsequent 7 residues of beta-galactosidase producing a catalytically active beta galactosidase fusion protein in which the amino-terminal methionine is ligated in frame with a histidine tag; and the like.

Similarly, in yeast, such as *Saccharomyces cerevisiae*, a number of vectors containing constitutive or inducible promoters such as alpha factor, alcohol oxidase and PGH can be used for production of the desired expression products. In mammalian host cells, a number of expression systems, including both plasmids and viral-based systems, can be utilized.

A host cell is optionally chosen for its ability to modulate the expression of the inserted sequences or to process the expressed protein in the desired fashion. Such modifications of the protein include, but are not limited to, glycosylation, acetylation, carboxylation, phosphorylation, lipidation, acylation etc. Post-translational processing for example, which cleaves a precursor form into a mature form of the protein (for example, by a furin protease) is optionally performed in the context of the host cell. Different host cells such as 3T3, COS, CHO, HeLa, BHK, MDCK, 293, W138, etc. have specific cellular machinery and characteristic mechanisms for such post-translational activities and can be chosen to ensure the correct modification and processing of the introduced, foreign protein.

For long-term, high-yield production of recombinant antiviral MOMO30 or HEVAR protein, stable expression systems may be employed. For example, polynucleotides encoding an antiviral MOMO30 or HEVAR protein can be introduced into suitable host cells using expression vectors which contain viral origins of replication or endogenous expression elements and a selectable marker gene. Following the introduction of the vector, cells are allowed to grow for 1-2 days in an enriched media before they are switched to selective media. The purpose of the selectable marker is to confer resistance to selection and its presence allows growth and recovery of cells which successfully express the introduced sequences. For example, resistant groups or colonies of stably transformed cells can be proliferated using tissue culture techniques appropriate to the cell type. Host cells transformed with a nucleic acid encoding an antiviral MOMO30 or HEVAR protein are optionally cultured under conditions suitable for the expression and recovery of the encoded protein from cell culture.

Following transduction of a suitable host cell line and growth of the host cells to an appropriate cell density, the selected promoter is induced by appropriate means (e.g., temperature shift or chemical induction) and cells are cultured for an additional period. The secreted protein product is then recovered from the culture medium. Alternatively, cells can be harvested by centrifugation, disrupted by physical or chemical means and the resulting crude extract retained for further purification. Eukaryotic or microbial cells employed in expression of proteins can be disrupted by any convenient method, including freeze-thaw cycling, sonication, mechanical disruption or use of cell lysing agents or other methods, which are well known to those skilled in the art.

Expressed antiviral MOMO30 or HEVAR proteins can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems noted herein), hydroxylapatite chromatography and lectin chromatography. The MOMO30 or HEVAR protein is unusually heat stable; this suggests that application of heat to denature such proteins or homologs thereof may be a useful approach to protein purification. Protein refolding steps can be used, as desired, in completing configuration of the mature protein. Finally, high performance liquid chromatography (HPLC) can be employed in the final purification steps.

In certain examples, the nucleic acids are introduced into vectors suitable for introduction and expression in prokaryotic cells, e.g., *E. coli* cells. For example, a nucleic acid including a polynucleotide sequence that encodes a F2GF1 chimeric RSV antigen can be introduced into any of a variety of commercially available or proprietary vectors, such as the pET series of expression vectors (e.g., pET19b and pET21d). Expression of the coding sequence is inducible by IPTG, resulting in high levels of protein expression.

The polynucleotide sequence encoding the chimeric RSV antigen is transcribed under the phage T7 promoter. Alternate vectors, such as pURV22 that include a heat-inducible lambda pL promoter are also suitable.

The expression vector is introduced (e.g., by electroporation) into a suitable bacterial host. Numerous suitable strains of *E. coli* are available and can be selected by one of skill in the art (for example, the Rosetta and BL21 (DE3) strains have proven favorable for expression of recombinant vectors containing polynucleotide sequences that encode F2GF1 chimeric RSV antigens.

In another example, a polynucleotide sequence that encodes an antiviral product is introduced into insect cells using a baculovirus expression vector system (BEVS). Recombinant baculovirus capable of infecting insect cells can be generated using commercially available vectors, kits and/or systems, such as the BD BaculoGold system from BD BioScience. Briefly, the polynucleotide sequence encoding the antiviral product is inserted into the pAcSG2 transfer vector. Then, host cells SF9 (*Spodoptera frugiperda*) are co-transfected by pAcSG2-chimer plasmid and BD BaculoGold, containing the linearized genomic DNA of the baculovirus *Autographa californica* nuclear polyhedrosis virus (AcNPV). Following transfection, homologous recombination occurs between the pACSG2 plasmid and the Baculovirus genome to generate the recombinant virus. In one example, the antiviral product is expressed under the regulatory control of the polyhedrin promoter (pH). Similar transfer vectors can be produced using other promoters, such as the basic (Ba) and p10 promoters. Similarly, alternative insect cells can be employed, such as SF21 which is closely related to the SF9 and the High Five (Hi5) cell line derived from a cabbage looper, *Trichoplusia ni.*

Following transfection and induction of expression (according to the selected promoter and/or enhancers or other regulatory elements), the expressed proteins are recovered (e.g., purified or enriched) and renatured to ensure folding into a biologically active conformation.

In yet other embodiments, the antiviral products are expressed in vivo using viral or non-viral expression vectors. In some embodiments, the antiviral hevamine-related proteins are delivered from viral-derived expression vectors. Exemplary viral vectors may include or be derived from adeno-associated virus, adenovirus, herpesvirus, vaccinia virus, poliovirus, poxvirus, HIV virus, lentivirus, retrovirus, Sindbis and other RNA viruses and the like. Also preferred are any viral families which share the properties of these viruses which make them suitable for use as vectors. Retroviruses include Murine Moloney Leukemia virus (MMLV), HIV and other lentivirus vectors. Adenovirus vectors are relatively stable and easy to work with, have high titers and can be delivered in aerosol formulation and can transfect non-dividing cells. Poxviral vectors are large and have several sites for inserting genes, they are thermostable and can be stored at room temperature. Viral delivery systems typically utilize viral vectors having one or more genes removed and with and an exogenous gene and/or gene/promoter cassette being inserted into the viral genome in place of the removed viral DNA. The necessary functions of the removed gene(s) may be supplied by cell lines which have been engineered to express the gene products of the early genes in trans.

In other embodiments, nonviral delivery systems are utilized for delivery of plasmid vectors or other bioactive non nucleic acid agents using lipid formulations comprising, for example, liposomes, such as cationic liposomes (e.g., DOTMA, DOPE, DC-cholesterol) and anionic liposomes. Liposomes can be further conjugated to one or more proteins or peptides to facilitate targeting to a particular cell, if desired. Administration of a composition comprising a compound and a cationic liposome can be administered to the blood afferent to a target organ or inhaled into the respiratory tract to target cells of the respiratory tract. Furthermore, active agent(s) can be administered as a component of a microcapsule or nanoparticle that can be targeted to a cell type of interest using targeting moieties described herein or that can be designed for slow release of one or more active agent(s) in accordance with a predetermined rate of release or dosage.

In other embodiments, the nucleic acids may be delivered in vivo by electroporation, the technology for which is available from Genetronics, Inc. (San Diego, Calif.), as well as by means of a SONOPORATION machine (ImaRx Pharmaceutical Corp., Tucson, Ariz.).

The nucleic acids may be in solution or suspension (for example, incorporated into microparticles, liposomes or cells). These may be targeted to a particular cell type via antibodies, receptors or receptor ligands. Vehicles such as "stealth" and other antibody conjugated liposomes (including lipid mediated drug targeting to cells of interest), receptor mediated targeting of DNA through cell specific ligands or viral vectors targeting e.g., lymphoid, epithelial or endothelial cells. In general, receptors are involved in pathways of endocytosis, either constitutive or ligand induced. These receptors cluster in clathrin-coated pits, enter the cell via clathrin-coated vesicles, pass through an acidified endosome in which the receptors are sorted and then either recycle to the cell surface, become stored intracellularly or are degraded in lysosomes. The internalization pathways serve a variety of functions, such as nutrient uptake, removal of activated proteins, clearance of macromolecules, opportunistic entry of viruses and toxins, dissociation and degradation of ligand and receptor level regulation. Many receptors follow more than one intracellular pathway, depending on the cell type, receptor concentration, type of ligand, ligand valency and ligand concentration.

Pharmaceutical Compositions

As used herein the language "pharmaceutically acceptable carrier" is intended to include any and all solvents, solubilizers, fillers, stabilizers, binders, absorbents, bases, buffering agents, lubricants, controlled release, vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. See e.g., A. H. Kibbe Handbook of Pharmaceutical Excipients, 3rd ed. Pharmaceutical Press, London, UK (2000). Except insofar as any conventional media or agent is incompatible with the active compound, use thereof in the compositions is contemplated. Supplementary agents can also be incorporated into the compositions. In certain embodiments, the pharmaceutically acceptable carrier comprises serum albumin.

The pharmaceutical composition of the application is formulated to be compatible with its intended route of administration. Examples of routes of administration include parenteral, e.g., intrathecal, intra-arterial, intravenous, intradermal, subcutaneous, oral, transdermal (topical) and transmucosal administration.

Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose, pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor ELTM (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene, glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an antiviral peptide) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the hevamine-related products are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the pharmaceutical compositions are formulated into ointments, salves, gels, or creams as generally known in the art.

In certain embodiments, the pharmaceutical composition is formulated for sustained or controlled release of the active ingredients. Biodegradable, biocompatible polymers can be used, such as ethylene vinyl acetate, polyanhydrides, polyglycolic acid, collagen, polyorthoesters, and poly lactic acid. Methods for preparation of such formulations will be apparent to those skilled in the art. The materials can also be obtained commercially from e.g., Alza Corporation and Nova Pharmaceuticals, Inc. Liposomal suspensions (including liposomes targeted to infected cells with monoclonal antibodies to viral antigens) can also be used as pharmaceutically acceptable carriers.

It is especially advantageous to formulate oral or parenteral compositions in dosage unit form for ease of administration and uniformity of dosage. Suitable unit dosage forms include, but are not limited to powders, tablets, pills, capsules, lozenges, suppositories, patches, nasal sprays, injectables, implantable sustained-release formulations, lipid complexes, etc.

A "dosage unit form" refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the present application are dictated by and directly dependent on the unique characteristics of the active compound and the particular therapeutic effect to be achieved, and the limitations inherent in the art of compounding such an active compound for the treatment of individuals.

Toxicity and therapeutic efficacy of the antiviral product of the present application can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the present application, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. The pharmaceutical compositions can be included in a container, pack, or dispenser together with instructions for administration.

The present application is further illustrated by the following examples that should not be construed as limiting. The contents of all references, patents, and published patent applications cited throughout this application, as well as the Figures and Tables, are incorporated herein by reference.

EXAMPLES

Preparation of MOMO30-Containing Cell Extracts and Proteins

FIG. 1 shows an exemplary method for preparing a plant extract from e.g., dried *M. balsamina* plants for purifying MOMO30 or HEVAR protein. In one non-limiting embodiment, the method comprises the steps of: (a) forming an aqueous plant extract from a dried *M. balsamina* plant; (b) lysing plant cells therefrom so as to form an aqueous plant extract; (c) centrifuging the aqueous plant extract to remove debris and particulates and retaining the aqueous supernatant; (d) filtering the aqueous supernatant through a MW cutoff filter to sterilize and further purify the MOMO30 or HEVAR protein; and (e) eluting MOMO30 or HEVAR protein from the filter retentate into buffer for storage and/or use.

Identification of MOMO30 Protein Sequence

N-terminal Edman degradation sequencing was carried out to determine the amino terminal sequence of the MOMO30 protein. FIG. 2, panel A shows that MOMO30 protein comprises the predicted amino acid sequence of SEQ ID NO. 1. As shown in FIG. 2, panel B, the amino-terminal sequence is virtually identical to the mature amino-terminal sequence corresponding to several different isolates of a hevamine-A-related protein from *Prosopis alba*. Hevamines are members of several families of plant chitinases and lysozymes that are important for plant defense against pathogenic bacteria and fungi and belong to the family 18 glycosyl hydrolases. Hevamines are known to hydrolyze linear polysaccharide chains of chitin and peptidoglycan. As described above, the MOMO30 protein is heat stable and resistant to most proteases, including trypsin, which is used in most liquid chromatography with tandem mass spectrometry strategies.

Production of Anti-MOMO30 Antibodies and Detection of MOMO30 Protein

Based on the amino-terminal sequence of the MOMO30 protein, polyclonal antisera was generated in rabbits using a synthetic peptide containing the amino acid sequence in FIG. 2, panel B sequence. As shown in FIG. 2, panel C, Western blot analysis showed that the anti-MOMO30 antibody detects a 30 kDa protein from *M. balsamina* plant extracts, as expected.

MOMO30 Causes Hemagglutination

Co-pending U.S. patent application Ser. No. 16/718,994 characterizes various biochemical and functional properties associated with MOMO30, including its ability to bind multiple viruses, including HIV-1, SIV-1 and Ebola. As described in the co-pending application, MOMO30 appears to bind sugar groups on viral surface proteins suggesting that MOMO30 has properties reminiscent of lectins. Inasmuch as lectins have often been found to exhibit hemagglutinin activity, it was of interest to investigate whether MOMO30 exhibits hemagglutinin activity too. FIG. 3 shows the results of this analysis. In this case, purified MOMO30 protein was tested for its ability to agglutinate sheep red blood cells (RBCs). As shown in panel A, a 30 mg/mi stock solution at a dilution of 1:512 was found to cause hemagglutination, consistent with lectin-like activity.

MOMO30 Stimulates the Activation and Proliferation of T Cells

Figure 4:
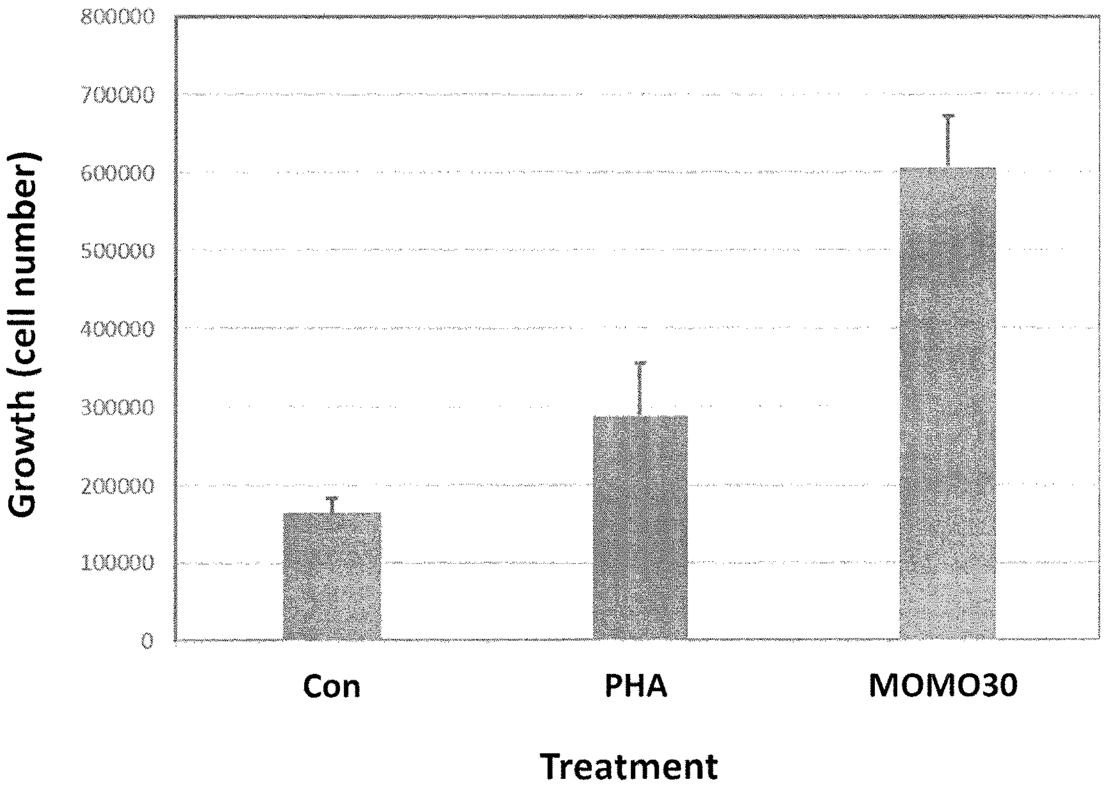
FIG. 4 shows that MOMO30 stimulates T cell growth. In each experiment, a fixed number of Jurkat cells was treated (left to right) with either PBS (control, Con), phytohemagglutinin A (PHA) or an equal amount of MOMO30.

Inasmuch as lectins are known to function as T cell mitogens, such as phytohemagglutinin A (PHA), it was of interest to examine whether MOMO30 can stimulate the activation and proliferation of T cells. Thus, a T cell activation assay was performed in which a fixed number of Jurkat cells was treated (left to right) with PBS (neg. control, Con), PHA (pos. control), or MOMO30 (FIG. 4). The results of this assay showed that MOMO30 similarly stimulates the activation and proliferation of T cells.

MOMO30 Exhibits Mannose-Sensitive Binding to Viral Cell Surface Proteins

Figure 5:
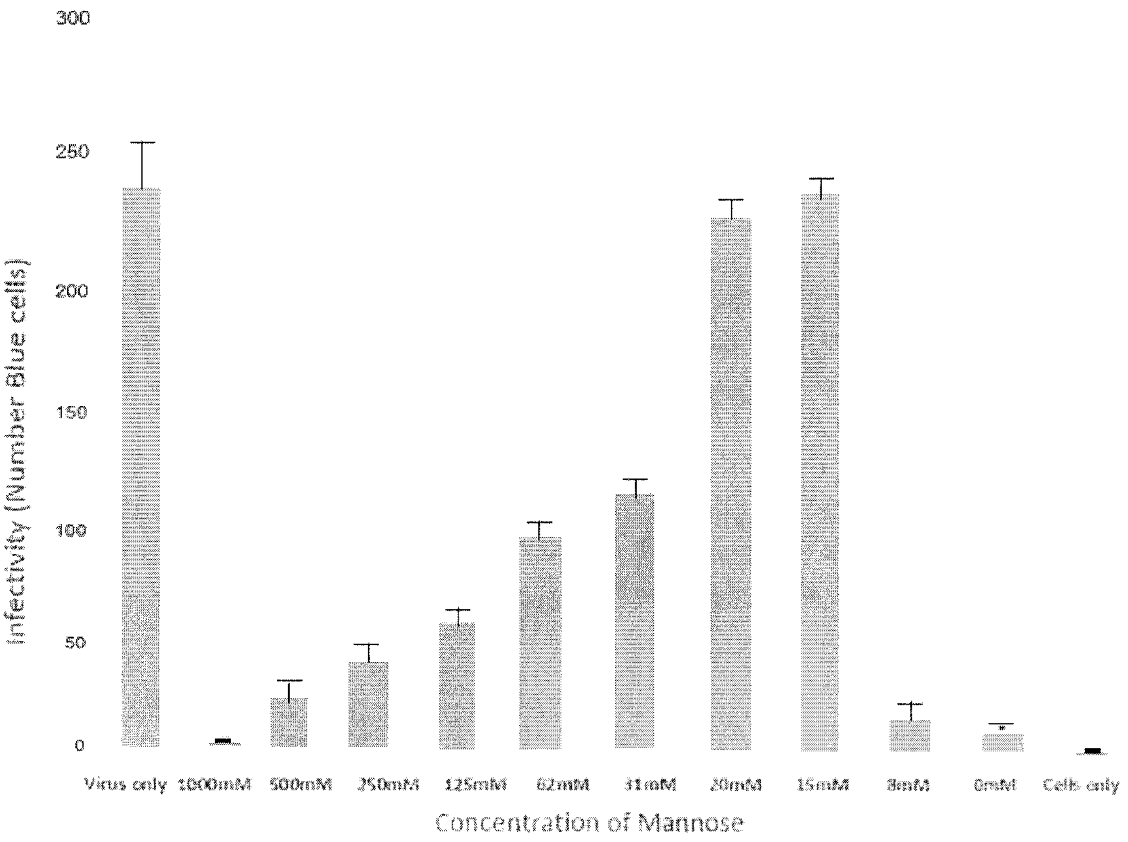
FIG. 5 depicts the results from a MAGI cell indicator assay using MOMO30-containing plant extract A in the presence of increasing concentrations of the monosaccharide mannose where higher bars indicate “inactivation” of the inhibitory effect.

Preliminary experiments showed that MOMO30 binds to HIV gp120 (data not shown). To further investigate the nature of the binding between the 30 kDa MOMO protein and gp120, MAGI indicator cells were infected with HIV in the presence of the plant extract at increasing concentrations of the monosaccharide mannose. HIV gp120 is known to undergo high-mannose glycosylation. The results of this analysis in FIG. 5 showed that while mannose concentrations of 15-20 mM virtually eliminated the ability of the MOMO30 protein in the extract to inhibit HIV infection, lower mannose concentrations had little effect on MOMO30's ability to inhibit HIV infection, and higher mannose concentrations had a progressively decreased ability to neutralize the inhibitory activity of MOMO30.

Figure 6A:
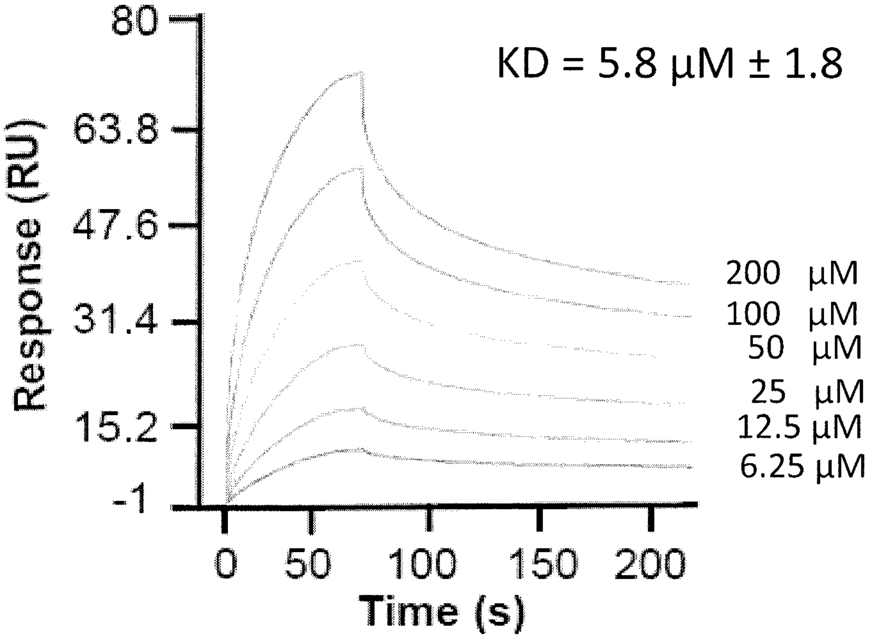
FIG. 6A shows a surface plasmon resonance (SPR) analysis (Biacore) indicating that MOMO30 protein from Extract A attaches to HIV gp120 so as to prevent its interaction with the CD4 receptor. Gp120 was immobilized on the gold surface and MOMO30 protein was flowed across the surface at concentrations from 6 to 200 nM. The assay was done in triplicate on separate days.
Figure 6B:
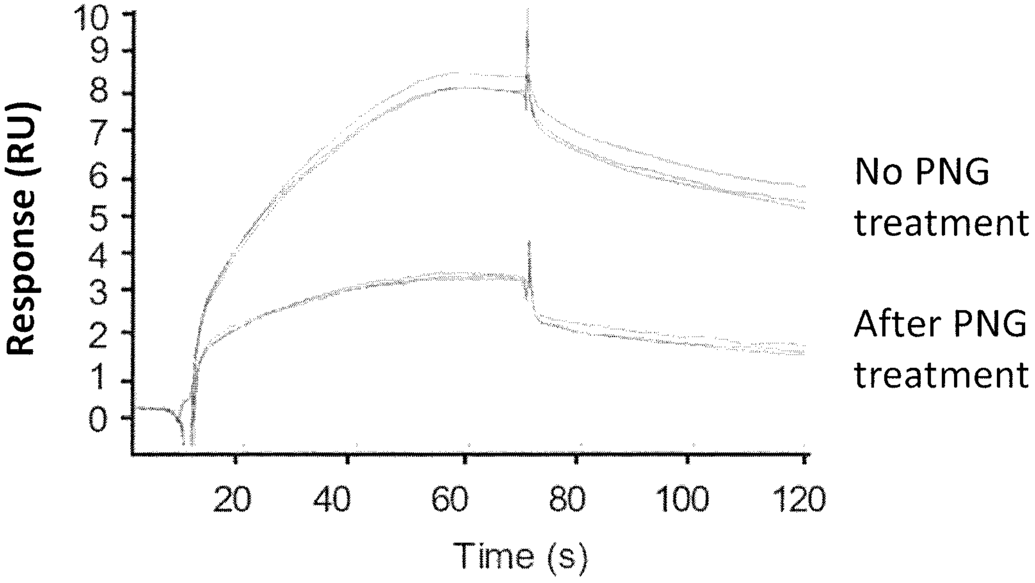
FIG. 6B shows that binding of MOMO30 to gp120 is dependent on glycosyl residues on gp120. A Biocore chip was saturated with gp120 and MOMO30 (top curves). The gp120-MOMO30 complexes were treated with PNG glycosylase to remove sugar residues from gp120 (bottom curves). Loss of sugar residues resulted in a decrease in binding.

To further examine the interaction between MOMO30 and purified gp120, surface plasmon resonance (Biacore) analysis was carried out. Gp120 was immobilized on the gold surface of a Biacore chip and increasing concentrations of MOMO30 protein (from 6.25 nM to 200 nM) were flowed across the surface and monitored by SPR. After 60 min, regeneration buffer as added to induce dissociation. The assay was done in triplicate on separate days. The results of this analysis are shown in FIG. 6A and indicate that MOMO30 bound to the surface in a concentration dependent manner with a KD of 5.8 μM±1.8. To further confirm that binding of MOMO30 to gp120 is dependent on glycosyl residues, such as mannose, on gp120, a Biocore chip was saturated with gp120 and MOMO30 to form gp120-MOMO30 complexes (FIG. 6B, top curves). The gp120-MOMO30 complexes were treated with PNGase F to remove sugar residues from gp120 (FIG. 6B, bottom curves). PNGase F is an amidase that works by cleaving between the innermost GleNAc and asparagine residues of high mannose, hybrid, and complex oligosaccharides from N-linked glycoproteins and glycopeptides, resulting in a deaminated protein or peptide and a free glycan. In this case, the loss of sugar residues produced a decrease in reflectance units (RU), which reflects a decrease in MOMO30 binding to gp120.

Evaluation of Chitinase Activity

Given that the N-terminal amino acid sequence of MOMO30 is consistent with properties shared by hevamines having chitinase properties, it was of interest to see whether the MOMO30 protein similarly exhibits chitinase activity. Thus, the Chitinase Microplate Assay Kit (MyBioSource, Inc., San Diego, Calif.) was employed according to the manufacturer's instructions. The results of this analysis confirm that MOMO30 has chitinase activity (data not shown).

Identification of the HEVAR Gene

To further identify hevamine-related sequences in *Momordica balsamina*, the following protocol was carried out: (1) isolate total plant RNA from *Momordica balsamina* leaves; (2) submit for RNAseq de novo transcriptome analysis (GeneWiz); (3) assemble reads in Trinity 2.5 software; (4) search for open reading frames (EMBOSS); (5) translate into protein sequences (Diamond BLASTx annotation); and (6) search protein sequences for hevamine-related sequence motifs.

As shown in FIG. 7, the results of this analysis identified a gene comprising the nucleotide coding sequence of SEQ ID NO: 12, which was translated using SnapGene software to reveal a hevamine-related protein (HEVAR) comprising the amino acid coding sequence of SEQ ID NO: 14 (top sequence) shown in FIG. 8.

A nucleic acid database search of the nucleotide coding sequence of SEQ ID NO: 12 identified a hevamine A-related nucleic acid sequence from *Momordica charantia* (NCBI Reference Sequence: XM_022291555.1; SEQ ID NO: 16) showing 93% identity to SEQ ID NO: 12. Further, as shown in FIG. 8, an alignment of the amino acid coding sequence of SEQ ID NO: 14 with the translation product (SEQ ID NO: 17, via SnapGene) of the *Momordica charantia* hevamine A-related nucleotide sequence in FIG. 7 shows 91% identity at the protein level.

As shown in FIG. 8, panel A, the HEVAR amino acid sequence of SEQ ID NO: 14 has a signal peptide sequence between amino acid numbers 1-31, which is removed in the secreted mature protein. FIG. 8, panel B shows the amino acid sequence of the mature HEVAR protein (SEQ ID NO: 15) in secreted form. The nucleotide sequence corresponding to the secreted form of HEVAR is set forth in SEQ ID NO: 13.

FIG. 9 shows an alignment of two conserved regions from the HEVAR protein relative to other hevamine A-related proteins comprising the amino acid sequences set forth in SEQ ID NOs: 18-26.

MOMO30 and HEVAR Binding to SARS-CoV-2 S Protein

The coronavirus (CoV) S protein mediates viral entry into host cells by first binding to a host receptor through the receptor-binding domain (RBD) in the S1 subunit and then fusing the viral and host membranes through the S2 subunit. Several binding assays may be used to confirm the ability of MOMO30 and HEVAR to bind coronavirus spike (S) proteins, including SARS-CoV-2 S protein and/or SARS-CoV-2 S1 subunit protein and determine the IC50 for MOMO30 and/or HEVAR (i.e., the concentration of MOMO30 or HEVAR which achieves a half-maximal inhibition). These assays may be evaluated for coronavirus binding activity using commercially available coronavirus reagents, cell lines and/or inhibitor screening assay kits.

The reagents and kits for these assays may utilize a variety of SARS-CoV-2 S protein, SARS-CoV-2 S1 subunit (receptor binding domain, RBD) protein-, and ACE2 protein reagents, which may be His-tagged, Fc-tagged, Avi-tagged, or biotin-labeled in order to facilitate detection of binding on microtiter plates and the like using suitable colorimetric or chemoluminescent substrates (BPS Bioscience, San Diego, Calif.).

In one embodiment, ACE2 protein is coated onto a 96-well microtiter plate and then incubated with a composition containing an aqueous MOMO30-containing plant extract, a HEVAR-containing plant extract, MOMO30 protein or HEVAR protein pre-incubated with His-, His-Avi- or Fc-tagged CoV-2 Spike (S) protein (or tagged versions of the S1 subunit protein), followed by recovery and detection of bound complexes using suitable detection reagents known in the art. The Avi-tag further allows for biotinylation of the CoV-2 fusion protein, which can facilitate binding to e.g., streptavidin-HRP conjugates for detection of binding.

Alternatively, His-, His-Avi- or Fc-tagged S protein or S1 protein is coated onto a 96-well microtiter plate and then incubated with a composition containing an aqueous MOMO30-containing plant extract, a HEVAR-containing plant extract, MOMO30 protein or HEVAR protein pre-incubated with His-, His-Avi- or Fc-tagged ACE2 protein, followed by recovery and detection of bound complexes using suitable detection reagents and conjugates known in the art.

In one embodiment, the MOMO30-containing plant extract, a HEVAR-containing plant extract, MOMO30 protein or HEVAR protein is incubated with purified CoV-2 spike (S) protein or purified CoV-2 receptor binding domain (RBD) and loaded on a non-denaturing polyacrylamide gel. The production of a band-shift compared to controls is consistent with binding of the MOMO30 or HEVAR protein to the S protein or S1 subunit.

In another embodiment, the MOMO30-containing plant extract, a HEVAR-containing plant extract, MOMO30 protein or HEVAR protein is evaluated for its ability to inhibit binding of purified fluorescently labeled CoV-2 S protein or CoV-2 S1 (RBD) subunit to its co-receptor ACE2 in ACE2-expressing cells. In this assay, purified fluorescently labeled CoV-2 S protein or CoV-2 S1 subunit is added to ACE2-expressing cells in the presence of increasing amounts of MOMO30 or HEVAR protein or a negative control (PBS only). Specific binding is shown by demonstrating that increasing concentrations MOMO30 or HEVAR protein lead to progressively less attachment of the fluorescently labeled CoV-2-S protein or CoV-2-S1 subunit to the ACE2 expressing cells.

In another embodiment, the interaction between MOMO30 or HEVAR protein and purified coronavirus S1 protein is evaluated by surface plasmon resonance (Biacore). In this assay, CoV-2-S protein or S1 protein is immobilized on the gold surface of a Biacore chip and increasing concentrations of MOMO30 or HEVAR protein (from e.g., 6.25 nM to 200 nM) are flowed across the surface and monitored by SPR. After 60 min, regeneration buffer is added to induce dissociation.

To confirm that MOMO30 or HEVAR protein binds to high mannose residues in CoV-2-S protein (or CoV-2-S1 subunit), a Biocore chip is saturated with CoV-2-S protein (or CoV-2-S1 subunit) and MOMO30 or HEVAR to form CoV-2-S protein-MOMO30- or HEVAR complexes. In addition, the CoV-2-S protein-MOMO30/HEVAR complexes can be treated with PNGase F to remove sugar residues from CoV-2-S protein (or CoV-2-S1 subunit). PNGase F is an amidase that works by cleaving between the innermost GlcNAc and asparagine residues of high mannose, hybrid, and complex oligosaccharides from N-linked glycoproteins and glycopeptides, resulting in a deaminated protein or peptide and a free glycan. In this case, the loss of sugar residues produces a decrease in reflectance units (RU), which reflects a decrease in MOMO30 or HEVAR binding to CoV-2-S protein. Reagents and cell lines for carrying out the above experiments may be obtained from BPS Bioscience (San Diego, Calif.) and Creative Biogene (Shirley, N.Y.).

Functional Activity of MOMO30- or HEVAR Containing Cell Extracts and Proteins

MOMO30- or HEVAR-containing cell extracts and/or proteins are tested for anti-SARS-CoV-2 activity using a functional assay evaluating the ability of MOMO30 or HEVAR to inhibit CoV-2 replication. The functional assays described below further allow for the generation of a dose-response curve reflecting the degree of CoV-2 inhibition, including an IC50 determination for MOMO30 or HEVAR.

In one embodiment, a MOMO30-containing plant extract, HEVAR-containing plant extract, purified MOMO30 protein or purified HEVAR protein is tested for inhibitory activity by an in vitro plaque reduction assay using SARS-CoV-2 infected Vero E6 cells, a monkey kidney cell line, which is known to express the ACE2 receptor. Briefly, Vero E6 cells are plated onto 12-well tissue culture plates and incubated overnight to allow for adherence to the plates. Serial dilutions of MOMO30 or HEVAR in cell maintenance media are then incubated with a defined amount of SARS-CoV-2 for one hour in the absence of Vero E6 cells. Negative control solutions include SARS-CoV-2 incubated for 1 hr in cell maintenance media without MOMO30, HEVAR or cells. Following the one hour incubation, the cell maintenance media is removed from the Vero E6 seeded plates and replaced with the pre-incubated solutions of MOMO30/SARS-CoV-2/cell media (test), HEVAR/SARS-CoV-2/cell media (test) and/or SARS-CoV-2/cell media (negative control). The cells are then incubated for 1 hr to allow adsorption of virus to the cells. Following the 1 hr incubation, the suspension is removed and methylcellulose overlays containing matched concentrations of MOMO30 or HEVAR are added to each well. The plates are incubated for 3 days, inactivated and then stained with crystal violet stain. Dose response curves are then generated based on the degree of replication inhibition in each well compared to the corresponding negative controls (i.e., absence of MOMO30 or HEVAR).

In another embodiment, a MOMO30- or HEVAR-containing plant extract or purified MOMO30 protein is tested for inhibitory activity using lentivirus-based, VSV-based or MuLV-based virus particles operably linked to a luciferase reporter that are pseudotyped with a CoV Spike (S) protein, such as SARS-CoV-2 S protein. More particularly, the assay evaluates the ability of MOMO30 or HEVAR to block expression of the luciferase reporter in ACE2-expressing cells infected with the S/S1-pseudotyped lentivirus reporter. A "bald" or non-pseudotyped control containing the luciferase reporter alone can be used as a negative control.

The ACE2-expressing cells or cell lines are infected with the pseudotyped or non-pseudotyped virus particles in the presence of increasing concentrations of MOMO30 or HEVAR. When using cells exhibiting low or no ACE2 expression, the pseudotyped and/or non-pseudotyped virus particles are co-infected with an expression construct, such replication-defective HIV-1 particles engineered to express human ACE2. A lentivirus-based luciferase reporter system for carrying out this assay includes pseudotyped (CoV-2 S protein) lentivirus reporters, non-pseudotyped lentivirus reporters (negative control), and ACE2-expressing lentiviruses (BPS Bioscience, San Diego, Calif., BPS #s 79942, 79943 and 79944). Additional reagents and cell lines for carrying out the above experiments may be obtained from BPS Bioscience (San Diego, Calif.) and Creative Biogene (Shirley, N.Y.).

To further confirm the binding of MOMO30 or HEVAR to high mannose residues in coronavirus S proteins, the above described functional assay may be carried out at increasing concentrations of the monosaccharide mannose. It is predicted that increasing mannose concentrations will progressively eliminate the ability of the MOMO30 or HEVAR protein to inhibit CoV-2 replication in Vero E6 cells and inhibit luciferase or β-gal expression from the reporter.

Efficacy Study of SARS CoV-2 Patients Treated with a MOMO30 or HEVAR Herbal Tea

In one embodiment, to evaluate of therapeutic efficacy of the MOMO30 or HEVAR protein, SARS CoV-2-infected patients are orally administered an herbal tea containing MOMO30 or HEVAR for a period of 6 months during which no other antiviral agents are administered. During this 6 month treatment period, the patients' viral loads and CD4+ lymphocyte counts are monitored. The results of this study are expected to show a significant reduction in average viral load accompanied by increased CD4+ cell counts increased over this same period.

In certain embodiments, to evaluate the therapeutic efficacy of the MOMO30 or HEVAR protein and facilitate a determination of effective dosages and administration protocols for the pharmaceutical compositions of the present application, an in vivo SARS-CoV-2 Syrian hamster model can be employed prior to human clinical trials. Use of this model can address key aspects of SARS-CoV-2 pathology following delivery of the protein or nucleic acid-based compositions of the present application, such as evaluation of viral loads and alleviation of the occurrence and severity of downstream effects, including the cytokine storm associated with SARS-CoV-2 infections. Syrian hamsters are permissive to SARS-CoV-2 and develop mild lung disease similar to the disease observed in early-stage COVID-19 patients.

Briefly, 6-8 week old female Syrian hamsters are anesthetized with ketamine/xylazine/atropine and inoculated intranasally (twice daily) with 50 μL containing about $1\times10^5$ $TCID_{50}$ (median tissue culture infectious dose) of a SARS-CoV-2 strain (day 0). Beginning 2 h before infection, animals are administered twice daily with a pharmaceutical composition described herein (positive control) and/or the pharmaceutically acceptable carrier(s) used in the pharmaceutical formulation (negative control). The pharmaceutical composition may be delivered orally, intranasally, by intratracheal instillation or by aerosol inhalation. Hamsters are monitored for appearance, behavior and weight. At day 2 post infection (pi) (day 3), 6 h following the 5th dose, hamsters are euthanized by IP injection of 500 μL Dolethal (200 mg/mL sodium pentobarbital, Vétoquinol SA). Lungs are collected and viral RNA and infectious virus are quantified by RT-qPCR and end-point virus titration, respectively. In addition, blood samples and lung tissue samples are collected and evaluated for cytokine levels and pharmacokinetic analysis of the HEVAR or MOMO30 protein of the present application. The results of these studies are expected to show at least a 2 or 3 $\log_{10}$ reduction in viral RNA copies per mg of lung tissue compared to the vehicle. Additionally, the results are expected to show a reduction of at least 10%, 20%, 50% or 80% in cytokine levels for one or more of IL-6, IL-1β, IL-2, IL-10, IFN-γ, TNF-α, and GM-CSF.

While various embodiments have been described above, it should be understood that such disclosures have been presented by way of example only and are not limiting. Thus, the breadth and scope of the subject compositions and methods should not be limited by any of the above-described exemplary embodiments, but should be defined only in accordance with the following claims and their equivalents.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. A method for treating or preventing a Severe Acute Respiratory Syndrome Corona Virus-2 (SARS-CoV-2) infection, comprising orally administering to a subject in need thereof a composition comprising: an effective amount hevamine related (HEVAR) protein which comprises an amino acid sequence that is at least 90% identical to SEQ ID NO: 15; and at least one pharmaceutically acceptable carrier.

2. The method of claim 1, wherein the amino acid sequence is 95%, 99% or 100% identical to SEQ ID NO: 15.

3. The method of claim 1, further comprising a second antiviral agent.

4. The method of claim 1, wherein the composition is in a dried form.

5. The method of claim 4, wherein the dried form comprises a capsule or tablet.

6. The method of claim 1, wherein the composition is in a liquid form.

7. The method of claim 1, wherein the composition comprises an herbal tea.

8. The method of claim 1, wherein the HEVAR protein is prepared by the steps of:

(a) drying a plant comprising HEVAR protein;

(b) extracting the dried plant in aqueous media;

(c) lysing cells from the extracted plant to form a plant cell lysate; and (d) centrifuging the plant cell lysate to remove debris and particulates to form a clarified plant cell lysate; and (e1) passing the plant cell lysate through a molecular weight cut-off filter and collecting the HEVAR-containing retentate, or (e2) purifying the HEVAR protein from the clarified plant cell lysate by immunoaffinity purification using an anti-HEVAR antibody.

9. A method for reducing or preventing the severity of the cytokine storm in a SARS-CoV-2 infected patient comprising: administering an effective amount of a pharmaceutical composition a pharmaceutical composition comprising an effective amount of a hevamine A-related plant protein which comprises an amino acid sequence that has at least 90% identical to SEQ ID NO: 15; and at least one pharmaceutically acceptable carrier, wherein the method results in at least a 20% reduction in cytokine levels for one or more of IL-6, IL-1β, IL-2, IL-10, IFN-γ, TNF-α, GM-CSF, or VEGF.

10. A pharmaceutical composition comprising:

a substantially pure HEVAR protein which comprises an amino acid sequence at least 95% or 99% identical to SEQ ID NO: 15; and at least one pharmaceutically acceptable carrier.

11. The composition of claim 10, wherein the HEVAR protein comprises the amino acid sequence of SEQ ID NO: 15.

12. The composition of claim 10, further comprising a second antiviral agent.

13. The composition of claim 10, wherein the composition comprises a capsule or tablet.

14. The composition of claim 10, wherein the composition is in a liquid form.

15. The composition of claim 10, wherein the composition comprises an herbal tea.

16. A method for treating or preventing a SARS-CoV-2 infection, comprising administering to a subject in need thereof a pharmaceutical composition comprising:

an effective amount of an expression vector operatively linked to a nucleic acid having a nucleotide sequence that is at least 95% identity to SEQ ID NO: 12 or SEQ ID NO: 13; and at least one pharmaceutically acceptable carrier.

17. The method of claim 16, wherein the nucleic acid comprises the nucleotide sequence of SEQ ID NO: 13.

18. The method of claim 16, wherein the expression vector is an adeno-associated virus vector.

19. The method of claim 16, wherein the pharmaceutical composition comprises a cell transformed with expression vector.

* * * * *

```
                    SEQUENCE LISTING

<160> NUMBER OF SEQ ID NOS: 26

<210> SEQ ID NO 1
<211> LENGTH: 16
<212> TYPE: PRT
<213> ORGANISM: Artificial Sequence
<220> FEATURE:
<223> OTHER INFORMATION: Synthetic-: N-terminal MOMO30
<220> FEATURE:
<221> NAME/KEY: misc_feature
<222> LOCATION: (12)..(12)
<223> OTHER INFORMATION: Xaa can be any naturally occurring amino acid

<400> SEQUENCE: 1

Gly Pro Ile Val Thr Tyr Trp Gly Gln Asn Val Xaa Glu Gly Glu Leu
1               5                   10                  15


<210> SEQ ID NO 2
<211> LENGTH: 80
<212> TYPE: PRT
<213> ORGANISM: Artificial Sequence
<220> FEATURE:
<223> OTHER INFORMATION: Synthetic: Hevamine A-like

<400> SEQUENCE: 2

Met Ser Ser Lys Thr Gln Ala Leu Val Leu Leu Leu Ser Pro Leu Leu
1               5                   10                  15

Leu Leu Ser His Leu Ser Ser Ser Gln Gly Cys Pro Ile Val Thr Tyr
            20                  25                  30

Trp Gly Gln Asn Val Asn Glu Gly Glu Leu Ser Thr Ala Cys Asp Thr
        35                  40                  45

Arg Lys Tyr Glu Ile Ile Asn Ile Ala Phe Met Asn Thr Phe Gly Asn
    50                  55                  60

Gly Gln Thr Pro Asn Ile Asp Leu Ser Gly His Cys Ser Glu Ser Trp
65                  70                  75                  80


<210> SEQ ID NO 3
<211> LENGTH: 80
<212> TYPE: PRT
<213> ORGANISM: Artificial Sequence
<220> FEATURE:
<223> OTHER INFORMATION: Synthetic: Hevamine A-like

<400> SEQUENCE: 3

Met Ala Ser Lys Thr Gln Ala Phe Val Leu Leu Leu Trp Pro Leu Leu
1               5                   10                  15

Leu Leu Ser His Leu Ser Ser Ser Gln Ser Cys Pro Ile Val Thr Tyr
            20                  25                  30

Trp Gly Gln Asn Val Asn Glu Gly Glu Leu Asp Ala Ala Cys Leu Thr
        35                  40                  45

Lys Arg Tyr Glu Ile Ile Asn Ile Ala Phe Met Asn Thr Phe Gly Asn
    50                  55                  60
```

-continued

```
Gly Gln Thr Pro Asp Ile Asn Leu Ser Gly His Cys Ser Glu Ser Trp
65                  70                  75                  80


<210> SEQ ID NO 4
<211> LENGTH: 80
<212> TYPE: PRT
<213> ORGANISM: Artificial Sequence
<220> FEATURE:
<223> OTHER INFORMATION: Synthetic: Hevamine A-like

<400> SEQUENCE: 4

Met Ser Tyr Lys Thr Gln Ala Leu Val Leu Leu Leu Ser Pro Leu Leu
1               5                   10                  15

Leu Leu Ser His Leu Ser Ser Ser Gln Gly Cys Pro Ile Val Thr Tyr
            20                  25                  30

Trp Gly Gln Asn Val Asn Glu Gly Glu Leu Ser Thr Ala Cys Asp Thr
        35                  40                  45

Gly Lys Tyr Glu Ile Ile Asn Ile Ala Phe Met Asn Thr Phe Gly Asn
    50                  55                  60

Gly Gln Thr Pro Asn Ile Asp Leu Ser Gly His Cys Ser Glu Ser Trp
65                  70                  75                  80


<210> SEQ ID NO 5
<211> LENGTH: 80
<212> TYPE: PRT
<213> ORGANISM: Artificial Sequence
<220> FEATURE:
<223> OTHER INFORMATION: Synthetic: Hevamine A-like

<400> SEQUENCE: 5

Met Ser Ser Lys Thr Gln Ala Leu Val Leu Leu Leu Ser Pro Leu Leu
1               5                   10                  15

Leu Leu Ser His Leu Ser Ser Ser Gln Gly Tyr Pro Ile Val Thr Tyr
            20                  25                  30

Trp Gly Gln Asn Val Asn Glu Gly Glu Leu Ser Thr Ala Cys Asp Thr
        35                  40                  45

Gly Lys Tyr Glu Ile Ile Asn Ile Ala Phe Met Asn Thr Phe Gly Asn
    50                  55                  60

Gly Gln Thr Pro Asn Ile Asp Leu Ser Gly His Cys Ser Glu Ser Trp
65                  70                  75                  80


<210> SEQ ID NO 6
<211> LENGTH: 80
<212> TYPE: PRT
<213> ORGANISM: Artificial Sequence
<220> FEATURE:
<223> OTHER INFORMATION: Synthetic: Hevamine A-like

<400> SEQUENCE: 6

Met Ser Ser Lys Thr Gln Ala Leu Val Leu Leu Leu Ser Pro Leu Leu
1               5                   10                  15

Leu Leu Ser His Leu Ser Ser Ser Gln Gly Cys Pro Ile Val Thr Tyr
            20                  25                  30

Trp Gly Gln Asn Val Asn Glu Gly Glu Leu Ser Thr Ala Cys Asp Thr
        35                  40                  45

Gly Lys Tyr Glu Ile Ile Asn Ile Ala Phe Met Asn Thr Phe Gly Asn
    50                  55                  60

Gly Gln Thr Pro Asp Ile Asn Leu Ala Gly His Cys Ser Ala Ser Trp
65                  70                  75                  80
```

-continued

<210> SEQ ID NO 7
<211> LENGTH: 80
<212> TYPE: PRT
<213> ORGANISM: Artificial Sequence
<220> FEATURE:
<223> OTHER INFORMATION: Synthetic: Hevamine A-like

<400> SEQUENCE: 7

```
Met Ala Ser Lys Thr Gln Ala Leu Val Leu Leu Leu Trp Pro Leu Met
1               5                   10                  15

Leu Leu Ser His Leu Ser Ser Ser Gln Ser Cys Pro Ile Val Thr Tyr
            20                  25                  30

Trp Gly Gln Asn Val Asn Glu Gly Glu Leu Asp Ala Ala Cys Gln Thr
        35                  40                  45

Glu Lys Tyr Glu Ile Ile Asn Ile Ala Phe Met Asn Thr Phe Gly Asn
    50                  55                  60

Gly Gln Thr Pro Asp Ile Asn Leu Ala Gly His Cys His Trp Ser Trp
65                  70                  75                  80
```

<210> SEQ ID NO 8
<211> LENGTH: 63
<212> TYPE: PRT
<213> ORGANISM: Artificial Sequence
<220> FEATURE:
<223> OTHER INFORMATION: Synthetic: Hevamine A-like

<400> SEQUENCE: 8

```
Met Ser Ser Lys Thr Gln Ala Leu Val Leu Leu Leu Ser Pro Leu Leu
1               5                   10                  15

Leu Leu Ser His Leu Ser Ser Ser Gln Gly Cys Pro Ile Val Thr Tyr
            20                  25                  30

Trp Gly Gln Asn Val Asn Glu Gly Glu Leu Ser Thr Phe Gly Asn Gly
        35                  40                  45

Gln Thr Pro Asp Ile Asn Leu Ala Gly His Cys Tyr Ala Ser Trp
    50                  55                  60
```

<210> SEQ ID NO 9
<211> LENGTH: 80
<212> TYPE: PRT
<213> ORGANISM: Artificial Sequence
<220> FEATURE:
<223> OTHER INFORMATION: Synthetic: Hevamine A-like

<400> SEQUENCE: 9

```
Met Ala Ser Lys Thr Gln Ala Leu Val Leu Leu Leu Trp Pro Leu Leu
1               5                   10                  15

Leu Leu Ser His Leu Ser Ser Ser Gln Ser Cys Pro Ile Val Thr Tyr
            20                  25                  30

Trp Gly Gln Asn Val Asn Glu Gly Glu Leu Asp Ala Ala Cys Gln Thr
        35                  40                  45

Lys Lys Tyr Glu Ile Ile Asn Ile Ala Phe Met Asn Thr Phe Gly Asn
    50                  55                  60

Gly Gln Thr Pro Asp Ile Asn Leu Ala Gly His Cys Ser Ala Ser Trp
65                  70                  75                  80
```

<210> SEQ ID NO 10
<211> LENGTH: 80
<212> TYPE: PRT
<213> ORGANISM: Artificial Sequence
<220> FEATURE:
<223> OTHER INFORMATION: Synthetic: Hevamine A-like -continued

<400> SEQUENCE: 10

```
Met Ala Ser Lys Thr Gln Ala Leu Val Leu Leu Leu Trp Pro Leu Leu
1               5                   10                  15

Leu Leu Ser His Leu Ser Ser Ser Gln Ser Cys Pro Ile Val Thr Tyr
            20                  25                  30

Trp Gly Gln Asn Val Asn Glu Gly Glu Leu Asp Ala Ala Cys Gln Thr
        35                  40                  45

Lys Lys Tyr Glu Ile Ile Asn Ile Ala Phe Met Asn Thr Phe Gly Asn
    50                  55                  60

Gly Gln Thr Pro Asp Ile Asn Leu Ala Gly His Cys His Trp Ser Ser
65                  70                  75                  80
```

<210> SEQ ID NO 11
<211> LENGTH: 80
<212> TYPE: PRT
<213> ORGANISM: Artificial Sequence
<220> FEATURE:
<223> OTHER INFORMATION: Synthetic: Hevamine A-like

<400> SEQUENCE: 11

```
Met Ala Ser Lys Pro Gln Ala Leu Val Leu Leu Leu Trp Pro Leu Leu
1               5                   10                  15

Leu Leu Ser His Leu Ser Ser Ser Leu Ser Cys Pro Ile Val Thr Tyr
            20                  25                  30

Trp Gly Lys Asn Val Asn Glu Gly Glu Leu Asp Ala Ala Cys Gln Thr
        35                  40                  45

Lys Lys Tyr Glu Ile Ile Asn Ile Ala Phe Met Asn Thr Phe Gly Asn
    50                  55                  60

Gly Gln Thr Pro Asp Ile Asn Leu Ala Gly His Cys His Trp Ser Trp
65                  70                  75                  80
```

<210> SEQ ID NO 12
<211> LENGTH: 921
<212> TYPE: DNA
<213> ORGANISM: M. balsamina
<220> FEATURE:
<221> NAME/KEY: misc_feature
<222> LOCATION: (1)..(921)
<223> OTHER INFORMATION: M. balsamina HEVR coding sequence

<400> SEQUENCE: 12

```
atggaatctc aattttgttc ttcatttcca tgttttattc tcctcgtaat tttccctttt     60

atgggctatt attccgaagc aataattacc ggcggcggaa ttgcgactta ttggggccag    120

gacacgagag agggccgact gaccgccgcc tgcgccaccg gaaaatttca gatcatcaac    180

atagggttcc tctctacatt cggcaacggc cggccgccgc aagtgaacct aacgcgccac    240

tgcagtccca tctccaacgg ttgccggaat gtgagcgtcg gcgtcctcaa ctgccgaaac    300

gacggcgtta aagtcatgct ctccatcggt ggccctcatg gaagctactc cctctcctcc    360

gccgccgaag ccattgacct tgctgactac atctggaaca attttctcgg tggccgctcc    420

acgtcactac gaccattcgg tgatgtgcca ttggacggcg tagatttcag gattgaacga    480

ggtcagtttt cccactatta cactatggtt gctcggcggc tacacgacta tggtcgacaa    540

tgtagtcgta aagtgtacct aacggcggct ccaggttgcc gttttccaga caagtaccta    600

accgaattgc ttcacactgg acttttcgac tatgtttggg ttagattttt tgacgatcga    660

caatgccaat ataattctgt taacccgtct ggcttttggt ggtcgtggat gcggtggata    720
```

aattcaattc cggcgaggaa attttacgtg ggaattcctg catctgaaga agccggagat 780
gggtacgtgg caccagaggt gttgataaag gaagtattgc cctttactaa gaagtttacc 840
aattacggtg gcgttatgct tttcgacttg tcgaatgatg ttcaaactaa ctacagttct 900
ataattagca atagggtttg a 921

<210> SEQ ID NO 13
<211> LENGTH: 829
<212> TYPE: DNA
<213> ORGANISM: M. balsamina
<220> FEATURE:
<221> NAME/KEY: misc_feature
<222> LOCATION: (1)..(829)
<223> OTHER INFORMATION: M. balsamina HEVR coding sequence

<400> SEQUENCE: 13
cggcggaatt gcgacttatt ggggccagga cacgagagag ggccgactga ccgccgcctg 60
cgccaccgga aaatttcaga tcatcaacat agggttcctc tctacattcg gcaacggccg 120
gccgccgcaa gtgaacctaa cgcgccactg cagtcccatc tccaacggtt gccggaatgt 180
gagcgtcggc gtcctcaact gccgaaacga cggcgttaaa gtcatgctct ccatcggtgg 240
ccctcatgga agctactccc tctcctccgc cgccgaagcc attgaccttg ctgactacat 300
ctggaacaat ttctcggtgg gccgctccac gtcactacga ccattcggtg atgtgccatt 360
ggacggcgta gatttcagga ttgaacgagg tcagttttcc cactattaca ctatggttgc 420
tcggcggcta cacgactatg gtcgacaatg tagtcgtaaa gtgtacctaa cggcggctcc 480
aggttgccgt tttccagaca agtacctaac cgaattgctt cacactggac ttttcgacta 540
tgtttgggtt agattttttg acgatcgaca atgccaatat aattctgtta acccgtctgg 600
cttttggtgg tcgtggatgc ggtggataaa ttcaattccg gcgaggaaat tttacgtggg 660
aattcctgca tctgaagaag ccggagatgg gtacgtggca ccagaggtgt tgataaagga 720
agtattgccc tttactaaga agtttaccaa ttacggtggc gttatgcttt tcgacttgtc 780
gaatgatgtt caaactaact acagttctat aattagcaat agggtttga 829

<210> SEQ ID NO 14
<211> LENGTH: 306
<212> TYPE: PRT
<213> ORGANISM: M. balsamina
<220> FEATURE:
<221> NAME/KEY: misc_feature
<222> LOCATION: (1)..(306)
<223> OTHER INFORMATION: M. balsamina HEVR preprotein sequence

<400> SEQUENCE: 14

Met Glu Ser Gln Phe Cys Ser Ser Phe Pro Cys Phe Ile Leu Leu Val
1 5 10 15

Ile Phe Pro Phe Met Gly Tyr Tyr Ser Glu Ala Ile Ile Thr Gly Gly
20 25 30

Gly Ile Ala Thr Tyr Trp Gly Gln Asp Thr Arg Glu Gly Arg Leu Thr
35 40 45

Ala Ala Cys Ala Thr Gly Lys Phe Gln Ile Ile Asn Ile Gly Phe Leu
50 55 60

Ser Thr Phe Gly Asn Gly Arg Pro Pro Gln Val Asn Leu Thr Arg His
65 70 75 80

Cys Ser Pro Ile Ser Asn Gly Cys Arg Asn Val Ser Val Gly Val Leu
85 90 95

Asn Cys Arg Asn Asp Gly Val Lys Val Met Leu Ser Ile Gly Gly Pro

```
            100                 105                 110

His Gly Ser Tyr Ser Leu Ser Ser Ala Ala Glu Ala Ile Asp Leu Ala
        115                 120                 125

Asp Tyr Ile Trp Asn Asn Phe Leu Gly Gly Arg Ser Thr Ser Leu Arg
    130                 135                 140

Pro Phe Gly Asp Val Pro Leu Asp Gly Val Asp Phe Arg Ile Glu Arg
145                 150                 155                 160

Gly Gln Phe Ser His Tyr Tyr Thr Met Val Ala Arg Arg Leu His Asp
                165                 170                 175

Tyr Gly Arg Gln Cys Ser Arg Lys Val Tyr Leu Thr Ala Ala Pro Gly
            180                 185                 190

Cys Arg Phe Pro Asp Lys Tyr Leu Thr Glu Leu Leu His Thr Gly Leu
        195                 200                 205

Phe Asp Tyr Val Trp Val Arg Phe Phe Asp Asp Arg Gln Cys Gln Tyr
    210                 215                 220

Asn Ser Val Asn Pro Ser Gly Phe Trp Trp Ser Trp Met Arg Trp Ile
225                 230                 235                 240

Asn Ser Ile Pro Ala Arg Lys Phe Tyr Val Gly Ile Pro Ala Ser Glu
                245                 250                 255

Glu Ala Gly Asp Gly Tyr Val Ala Pro Glu Val Leu Ile Lys Glu Val
            260                 265                 270

Leu Pro Phe Thr Lys Lys Phe Thr Asn Tyr Gly Gly Val Met Leu Phe
        275                 280                 285

Asp Leu Ser Asn Asp Val Gln Thr Asn Tyr Ser Ser Ile Ile Ser Asn
    290                 295                 300

Arg Val
305


<210> SEQ ID NO 15
<211> LENGTH: 275
<212> TYPE: PRT
<213> ORGANISM: M. balsamina
<220> FEATURE:
<221> NAME/KEY: misc_feature
<222> LOCATION: (1)..(275)
<223> OTHER INFORMATION: M. balsamina HEVR mature protein sequence

<400> SEQUENCE: 15

Gly Gly Ile Ala Thr Tyr Trp Gly Gln Asp Thr Arg Glu Gly Arg Leu
1               5                   10                  15

Thr Ala Ala Cys Ala Thr Gly Lys Phe Gln Ile Ile Asn Ile Gly Phe
            20                  25                  30

Leu Ser Thr Phe Gly Asn Gly Arg Pro Pro Gln Val Asn Leu Thr Arg
        35                  40                  45

His Cys Ser Pro Ile Ser Asn Gly Cys Arg Asn Val Ser Val Gly Val
    50                  55                  60

Leu Asn Cys Arg Asn Asp Gly Val Lys Val Met Leu Ser Ile Gly Gly
65                  70                  75                  80

Pro His Gly Ser Tyr Ser Leu Ser Ser Ala Ala Glu Ala Ile Asp Leu
                85                  90                  95

Ala Asp Tyr Ile Trp Asn Asn Phe Leu Gly Gly Arg Ser Thr Ser Leu
            100                 105                 110

Arg Pro Phe Gly Asp Val Pro Leu Asp Gly Val Asp Phe Arg Ile Glu
        115                 120                 125

Arg Gly Gln Phe Ser His Tyr Tyr Thr Met Val Ala Arg Arg Leu His
    130                 135                 140
```

```
Asp Tyr Gly Arg Gln Cys Ser Arg Lys Val Tyr Leu Thr Ala Ala Pro
145                 150                 155                 160

Gly Cys Arg Phe Pro Asp Lys Tyr Leu Thr Glu Leu Leu His Thr Gly
                165                 170                 175

Leu Phe Asp Tyr Val Trp Val Arg Phe Phe Asp Asp Arg Gln Cys Gln
            180                 185                 190

Tyr Asn Ser Val Asn Pro Ser Gly Phe Trp Trp Ser Trp Met Arg Trp
        195                 200                 205

Ile Asn Ser Ile Pro Ala Arg Lys Phe Tyr Val Gly Ile Pro Ala Ser
    210                 215                 220

Glu Glu Ala Gly Asp Gly Tyr Val Ala Pro Glu Val Leu Ile Lys Glu
225                 230                 235                 240

Val Leu Pro Phe Thr Lys Lys Phe Thr Asn Tyr Gly Gly Val Met Leu
                245                 250                 255

Phe Asp Leu Ser Asn Asp Val Gln Thr Asn Tyr Ser Ser Ile Ile Ser
            260                 265                 270

Asn Arg Val
        275


<210> SEQ ID NO 16
<211> LENGTH: 921
<212> TYPE: DNA
<213> ORGANISM: M. charantia
<220> FEATURE:
<221> NAME/KEY: misc_feature
<222> LOCATION: (1)..(921)
<223> OTHER INFORMATION: M. charantia hevamine A-like coding region
      sequence

<400> SEQUENCE: 16

atggaatctc aattttgttc ttcatttcca cgttttcttc tcctcataat tctcgcttct      60

atattgggtt gttattcgga agcaattacc ggcggcggaa ttgccactta ctggggccag     120

aacacgagag agggccggct gaccgccgcc tgcgccaccg gaaaatttca gatcatcaac     180

atagggttcc tctctacatt cggcaacggc cggccgccgc aagtgaacct aacgcgccac     240

tgcagtcccg tctccaacgg ctgccggaat gtgagcgttg gcgtcctcaa ctgccgaaac     300

gatggcgtta aagtcatgct ctccattggt ggccctcacg gaagctactt cctctcctcc     360

gccgccgaag ccgttgacct tgctgactac atctggaaca acttcctcgg cggccactcc     420

acgtcactac gaccgtttgg tgatgtacca ttggacggtg tagatttcag gattgagcga     480

gtcgagttct cccactacta cgccatggtt gctcggcggc tacacgacta tggccggcaa     540

agtaaccgta aagtgtactt aacggcggct ccggggtgcc gttttcccga caaataccta     600

actgaatcgc ttcacactgg acttttcgac tatgtttggg ttagattttt tgacgaccgg     660

caatgccgtt atgattccgt taacccgtcg ggcttttggt ggtcgtggat gcggtggaca     720

cattcaattc cggcgaggaa attttacttg ggaattccgg catccgaaga agccggagat     780

gggtacgtgg caccggaggt gctgataaag gaagtgctgc cgtttgttaa gaggttcaca     840

agttatggcg gcgttatgct tttcgacttg tcgaatgatg ttcaaactaa ctacagttct     900

ataattagca atagggtttg a                                               921


<210> SEQ ID NO 17
<211> LENGTH: 306
<212> TYPE: PRT
<213> ORGANISM: M. charantia
<220> FEATURE:
```

<221> NAME/KEY: misc_feature
<222> LOCATION: (1)..(306)
<223> OTHER INFORMATION: M. charantia hevamine A-like preprotein
sequence

<400> SEQUENCE: 17

```
Met Glu Ser Gln Phe Cys Ser Ser Phe Pro Arg Phe Leu Leu Leu Ile
1               5                   10                  15

Ile Leu Ala Ser Ile Leu Gly Cys Tyr Ser Glu Ala Ile Thr Gly Gly
            20                  25                  30

Gly Ile Ala Thr Tyr Trp Gly Gln Asn Thr Arg Glu Gly Arg Leu Thr
        35                  40                  45

Ala Ala Cys Ala Thr Gly Lys Phe Gln Ile Ile Asn Ile Gly Phe Leu
    50                  55                  60

Ser Thr Phe Gly Asn Gly Arg Pro Pro Gln Val Asn Leu Thr Arg His
65                  70                  75                  80

Cys Ser Pro Val Ser Asn Gly Cys Arg Asn Val Ser Val Gly Val Leu
                85                  90                  95

Asn Cys Arg Asn Asp Gly Val Lys Val Met Leu Ser Ile Gly Gly Pro
            100                 105                 110

His Gly Ser Tyr Phe Leu Ser Ser Ala Ala Glu Ala Val Asp Leu Ala
        115                 120                 125

Asp Tyr Ile Trp Asn Asn Phe Leu Gly Gly His Ser Thr Ser Leu Arg
    130                 135                 140

Pro Phe Gly Asp Val Pro Leu Asp Gly Val Asp Phe Arg Ile Glu Arg
145                 150                 155                 160

Val Glu Phe Ser His Tyr Tyr Ala Met Val Ala Arg Arg Leu His Asp
                165                 170                 175

Tyr Gly Arg Gln Ser Asn Arg Lys Val Tyr Leu Thr Ala Ala Pro Gly
            180                 185                 190

Cys Arg Phe Pro Asp Lys Tyr Leu Thr Glu Ser Leu His Thr Gly Leu
        195                 200                 205

Phe Asp Tyr Val Trp Val Arg Phe Phe Asp Asp Arg Gln Cys Arg Tyr
    210                 215                 220

Asp Ser Val Asn Pro Ser Gly Phe Trp Trp Ser Trp Met Arg Trp Thr
225                 230                 235                 240

His Ser Ile Pro Ala Arg Lys Phe Tyr Leu Gly Ile Pro Ala Ser Glu
                245                 250                 255

Glu Ala Gly Asp Gly Tyr Val Ala Pro Glu Val Leu Ile Lys Glu Val
            260                 265                 270

Leu Pro Phe Val Lys Arg Phe Thr Ser Tyr Gly Gly Val Met Leu Phe
        275                 280                 285

Asp Leu Ser Asn Asp Val Gln Thr Asn Tyr Ser Ser Ile Ile Ser Asn
    290                 295                 300

Arg Val
305
```

<210> SEQ ID NO 18
<211> LENGTH: 17
<212> TYPE: PRT
<213> ORGANISM: Artificial Sequence
<220> FEATURE:
<223> OTHER INFORMATION: Synthetic: Hevamine A-like

<400> SEQUENCE: 18

```
Lys Val Met Leu Ser Leu Gly Gly Leu Asp Gly Ile Asp Phe Asp Ile
1               5                   10                  15
```

Glu

<210> SEQ ID NO 19
<211> LENGTH: 17
<212> TYPE: PRT
<213> ORGANISM: Artificial Sequence
<220> FEATURE:
<223> OTHER INFORMATION: Synthetic: Hevamine A-like

<400> SEQUENCE: 19

Lys Val Leu Leu Ser Ile Gly Gly Leu Asp Gly Val Asp Phe Asp Ile
1 5 10 15

Glu

<210> SEQ ID NO 20
<211> LENGTH: 17
<212> TYPE: PRT
<213> ORGANISM: Artificial Sequence
<220> FEATURE:
<223> OTHER INFORMATION: Synthetic: Hevamine A-like

<400> SEQUENCE: 20

Lys Val Met Leu Ser Leu Gly Gly Leu Asp Gly Ile Asp Phe Asp Ile
1 5 10 15

Glu

<210> SEQ ID NO 21
<211> LENGTH: 17
<212> TYPE: PRT
<213> ORGANISM: Artificial Sequence
<220> FEATURE:
<223> OTHER INFORMATION: Synthetic: Hevamine A-like

<400> SEQUENCE: 21

Lys Val Leu Leu Ser Ile Gly Gly Leu Asp Gly Val Asp Phe Asp Ile
1 5 10 15

Glu

<210> SEQ ID NO 22
<211> LENGTH: 17
<212> TYPE: PRT
<213> ORGANISM: Artificial Sequence
<220> FEATURE:
<223> OTHER INFORMATION: Synthetic: Hevamine A-like

<400> SEQUENCE: 22

Lys Thr Phe Leu Ser Ile Ala Gly Phe His Gly Leu Asp Leu Asp Trp
1 5 10 15

Glu

<210> SEQ ID NO 23
<211> LENGTH: 17
<212> TYPE: PRT
<213> ORGANISM: Artificial Sequence
<220> FEATURE:
<223> OTHER INFORMATION: Synthetic: Hevamine A-like

<400> SEQUENCE: 23

Lys Val Leu Leu Ser Leu Gly Gly Val Asp Gly Phe Asp Phe Asp Ile
1 5 10 15

Glu

-continued

```
<210> SEQ ID NO 24
<211> LENGTH: 17
<212> TYPE: PRT
<213> ORGANISM: Artificial Sequence
<220> FEATURE:
<223> OTHER INFORMATION: Synthetic: Hevamine A-like

<400> SEQUENCE: 24

Lys Ile Leu Pro Ser Ile Gly Gly Tyr Asp Gly Val Asp Ile Asp Trp
1               5                   10                  15

Glu


<210> SEQ ID NO 25
<211> LENGTH: 17
<212> TYPE: PRT
<213> ORGANISM: Artificial Sequence
<220> FEATURE:
<223> OTHER INFORMATION: Synthetic: Hevamine A-like

<400> SEQUENCE: 25

Lys Thr Ile Ile Ser Val Gly Gly Phe Asp Gly Val Asp Leu Asp Trp
1               5                   10                  15

Glu


<210> SEQ ID NO 26
<211> LENGTH: 17
<212> TYPE: PRT
<213> ORGANISM: Artificial Sequence
<220> FEATURE:
<223> OTHER INFORMATION: Synthetic: Hevamine A-like

<400> SEQUENCE: 26

Lys Phe Met Val Ala Val Gly Gly Phe Asp Gly Leu Asp Leu Asp Trp
1               5                   10                  15

Glu
```